United States Patent [19]

Ross et al.

[11] Patent Number: 5,317,023
[45] Date of Patent: May 31, 1994

[54] BENZOFURAN DERIVATIVES

[75] Inventors: Barry C. Ross; David Middlemiss; David I. C. Scopes; Torquil I. M. Jack; Kevin S. Cardwell; Michael D. Dowle; John G. Montana; Martin Pass; Duncan B. Judd, all of Ware, Great Britain

[73] Assignee: Glaxo Group Limited, London, England

[21] Appl. No.: 883,386

[22] Filed: May 15, 1992

[30] Foreign Application Priority Data

May 16, 1991 [GB] United Kingdom ............... 9110633
Jan. 22, 1992 [GB] United Kingdom ............... 9201358
Mar. 10, 1992 [GB] United Kingdom ............... 9205174

[51] Int. Cl.[5] .................. C07D 401/048; A61K 31/44
[52] U.S. Cl. ..................... 514/303; 546/118
[58] Field of Search .................. 546/118; 514/303

[56] References Cited

U.S. PATENT DOCUMENTS 4,880,804  11/1989  Carini et al. ............... 548/325

FOREIGN PATENT DOCUMENTS 0392317 10/1990 European Pat. Off. .
0399731 11/1990 European Pat. Off. .
0399732 11/1990 European Pat. Off. .
0400835 12/1990 European Pat. Off. .
0400974 12/1990 European Pat. Off. .
0415886  3/1991 European Pat. Off. .
0420237  4/1991 European Pat. Off. .
0425921  5/1991 European Pat. Off. .
0426021  5/1991 European Pat. Off. .
0430300  6/1991 European Pat. Off. .
0434038  6/1991 European Pat. Off. .
0434249  6/1991 European Pat. Off. .
0461040 12/1991 European Pat. Off. .
WO91/13063  9/1991 PCT Int'l Appl. .

Primary Examiner—Jerome D. Goldberg
Assistant Examiner—Phyllis Spivack
Attorney, Agent, or Firm—Bacon & Thomas

[57] ABSTRACT

The invention provides compounds of formula (I):

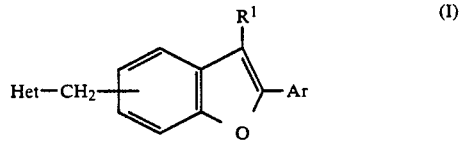

or a physiologically acceptable salt, solvate or metabolically labile ester thereof wherein
$R^1$ represents a hydrogen atom or a halogen atom or a group selected from $C_{1-6}$alkyl, $C_{2-6}$alkenyl, fluoro$C_{1-6}$alkyl, $C_{1-6}$alkoxy, —CHO, —$CO_2H$ or —$COR^2$;
Ar represents optionally substituted phenyl
Het represents the group

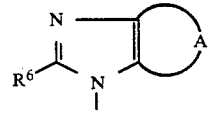

A represents

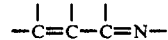

The compounds may be used in the treatment or prophylaxis of hypertension and diseases associated with cognitive disorders.

25 Claims, No Drawings

BENZOFURAN DERIVATIVES

This invention relates to benzofuran derivatives, processes for their preparation and pharmaceutical compositions containing them. According to a first aspect of the invention we provide a compound of the general formula (I):

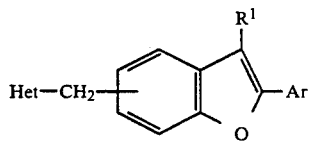

or a physiologically acceptable salt, solvate (e.g. hydrate) or metabolically labile ester thereof in which $R^1$ represents a hydrogen atom or a halogen atom or a group selected from $C_{1-6}$alkyl, $C_{2-6}$alkenyl, fluoro$C_{1-6}$alkyl, $C_{1-6}$alkoxy, —CHO, —$CO_2H$ or —$COR^2$;

Ar represents the group

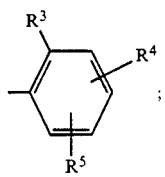

$R^2$ represents a group selected from $C_{1-6}$alkyl, $C_{2-6}$alkenyl, $C_{1-6}$alkoxy or the group —$NR^{15}R^{16}$;

$R^3$ represents a group selected from —$CO_2H$, —NHSO$_2$CF$_3$ or a C-linked tetrazolyl group;

$R^4$ and $R^5$ which may be the same or different each independently represent a hydrogen atom or a halogen atom or a $C_{1-6}$alkyl group;

Het represents the group

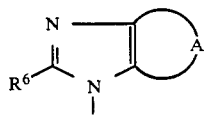

A, when read in a clockwise or anti-clockwise direction, represents a group selected from

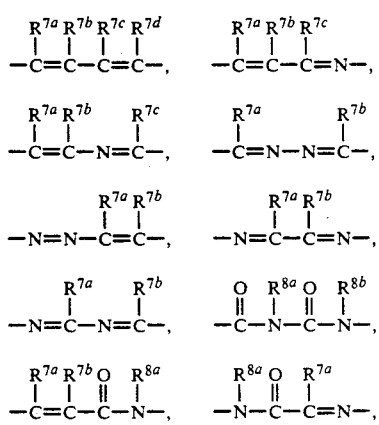

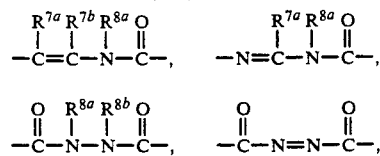

or

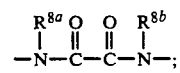

$R^6$ represents a hydrogen atom or a group selected from $C_{1-6}$alkyl, $C_{2-6}$alkenyl, $C_{1-6}$alkylthio, $C_{1-6}$alkoxy, $C_{3-7}$cycloalkyl, or $C_{3-7}$cycloalkyl$C_{1-4}$alkyl;

$R^{7a}$, $R^{7b}$, $R^{7c}$ and $R^{7d}$, which may be the same or different, each independently represents a hydrogen atom or a halogen atom or a group selected from cyano, nitro, $C_{1-6}$alkyl, $C_{2-6}$alkenyl, $C_{3-7}$cycloalkyl, $C_{3-7}$cycloalkyl$C_{1-4}$alkyl, fluoro$C_{1-6}$alkyl, —$(C_mH_{2m})R^9$, —$(CH_2)_nCOR^{10}$ or —$(CH_2)_pNR^{11}COR^{12}$;

$R^{8a}$ and $R^{8b}$, which may be the same or different, each independently represents a hydrogen atom or a group selected from $C_{1-6}$alkyl, $C_{3-6}$alkenyl, —$COR^{13}$, —$SO_2R^{13}$ or —$(CH_2)_qR^{14}$;

$R^9$ represents a hydroxy or $C_{1-6}$alkoxy group;

$R^{10}$ represents a hydrogen atom or a group selected from hydroxy, $C_{1-6}$alkyl, $C_{1-6}$alkoxy, phenyl, phenoxy or the group —$NR^{15}R^{16}$;

$R^{11}$ represents a hydrogen atom or a $C_{1-6}$alkyl group;

$R^{12}$ represents a hydrogen atom or a group selected from $C_{1-6}$alkyl, $C_{1-6}$alkoxy, phenyl, phenoxy, or the group —$NR^{15}R^{16}$;

$R^{13}$ represents a group selected from $C_{1-6}$alkyl, $C_{2-6}$alkenyl, $C_{1-6}$alkoxy or the group —$NR^{15}R^{16}$;

$R^{14}$ represents a group selected from hydroxy, $C_{1-6}$alkoxy, —$CO_2R^{17}$ or the group —$NR^{15}R^{16}$;

$R^{15}$ and $R^{16}$, which may be the same or different, each independently represent a hydrogen atom or a $C_{1-4}$alkyl group or —$NR^{15}R^{16}$ forms a saturated heterocyclic ring which has 5 or 6 ring members and may optionally contain in the ring one oxygen atom;

$R^{17}$ represents a hydrogen atom or a $C_{1-6}$alkyl group;

m represents an integer from 1 to 6;

n represents zero or an integer from 1 to 4;

p represents an integer from 1 to 4; and q represents an integer from 1 to 4.

Where the compound of general formula (I) is optically active, said formula (I) is intended to cover all enantiomers, diastereoisomers and mixtures thereof including racemates. Where a compound of the present invention contains one or more double bonds, these may exist in the cis or trans configuration. Furthermore, where such geometric isomers exist, formula (I) is intended to cover mixtures thereof.

The invention also includes within its scope the solvates, especially the hydrates of compounds of general formula (I).

Within the above definition the term 'alkyl', 'alkoxy' or 'alkylthio' as a group or part of a group means that the group is straight or branched. The term 'alkenyl' as a group or part of a group means that the group is straight or branched and contains at least one carbon-carbon double bond. Furthermore, it will be appreciated that when $R^{8a}$ or $R^{8b}$ represents a $C_{3-6}$alkenyl group, the carbon-carbon double bond shall not be in conjugation with the group represented by Het in general formula (I). The term 'cycloalkyl' as a group or part of a group may be, for example, a cyclopropyl, cyclobutyl, cyclopentyl or cyclohexyl group.

The term 'halogen' means a fluorine, chlorine, bromine or iodine atom.

The term 'fluoroC$_{1-6}$alkyl' means a C$_{1-6}$alkyl group in which one or more hydrogen atoms have been replaced by a fluorine atom, for example, —CH$_2$CF$_3$.

The term —(C$_m$H$_{2m}$)R$^9$ means a straight or branched alkyl group substituted at any of the carbon atoms in that group by a substituent represented by R$^9$, for example, —CH$_2$R$^9$, —CH$_2$CH$_2$R$^9$, —CH(CH$_3$)R$^9$ or —C(CH$_3$)$_2$R$^9$. Groups in which R$^9$ is located on the terminal carbon atom, for example, —CH$_2$R$^9$, —CH$_2$CH$_2$R$^9$ or —CH$_2$CH$_2$CH$_2$R$^9$, may also be represented herein by the group —(CH$_2$)$_m$R$^9$.

Within the above definition when —NR$^{15}$R$^{16}$ represents a saturated heterocyclic ring, this contains 5 or 6 ring members, one of which may be an oxygen atom. Suitable heterocyclic groups are a pyrrolidino, piperidino or morpholino group.

A particularly preferred class of compounds of general formula (I) is that wherein R$^6$ represents a hydrogen atom or a C$_{1-5}$alkyl, C$_{3-5}$alkenyl, C$_{1-5}$alkoxy, C$_{3-5}$cycloalkyl or C$_{3-5}$cycloalkylC$_{1-2}$alkyl group. Particularly preferred are those compounds wherein R$^6$ is a C$_{2-4}$alkyl group (especially an ethyl, n-propyl or n-butyl group).

A yet further preferred class of compounds of general formula (I) is that wherein R$^1$ represents a hydrogen atom or a halogen atom or a group selected from C$_{1-6}$alkyl, C$_{1-6}$alkoxy or fluoroC$_{1-6}$alkyl, and in particular a halogen atom, especially bromine.

Another preferred class of compounds of general formula (I) is that wherein A represents a group selected from

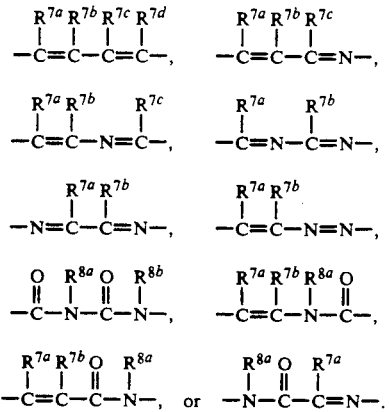

Particularly preferred are compounds of general formula (I) wherein a represents a group selected from

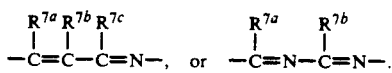

A further preferred class of compounds of general formula (I) is that wherein R$^{7a}$, R$^{7b}$, R$^{7c}$ and R$^{7d}$ each independently represent a hydrogen atom or a halogen atom or a group selected from C$_{1-6}$alkyl, C$_{3-7}$cycloalkyl, C$_{3-7}$cycloalkylC$_{1-4}$alkyl, —(CH$_2$)$_m$R$^9$ or —(CH$_2$)$_n$COR$^{10}$. In particular, R$^9$ represents a hydroxy or C$_{1-6}$alkoxy group, and preferably a hydroxy, methoxy, ethoxy, propoxy or butoxy group, and especially a hydroxy or methoxy group. R$^{10}$, in particular, represents a hydrogen atom or a hydroxy, C$_{1-6}$alkoxy or —NR$^{15}$R$^{16}$ group (especially wherein R$^{15}$ and R$^{16}$ each independently represent a hydrogen atom or a C$_{1-4}$alkyl group), and preferably a hydrogen atom or a hydroxy, methoxy, ethoxy, propoxy or butoxy group, and especially a hydrogen atom or a hydroxy or methoxy group, and m is 1 or 2 and n is zero, 1 or 2.

In a particularly preferred embodiment of the present invention, R$^{7a}$, R$^{7b}$, R$^{7c}$ and R$^{7d}$ each independently represent a hydrogen or chlorine atom or a group selected from methyl, ethyl, cyclopropyl, cyclopropylmethyl, —CH$_2$OH, —CH$_2$OCH$_3$, —CHO, —CO$_2$H, —CO$_2$CH$_3$, —CO$_2$CH$_2$CH$_3$, —CONH$_2$ and —CONHCH$_3$.

A yet further preferred class of compounds of general formula (I) is that wherein R$^{7a}$, R$^{7b}$, R$^{7c}$ and R$^{7d}$ each independently represent a hydrogen or chlorine atom or a group selected from methyl, ethyl, cyclopropyl, cyclopropylmethyl, —CH$_2$OH, —CH$_2$OCH$_3$, —CHO, —CO$_2$H, —CO$_2$CH$_3$, —CO$_2$CH$_2$CH$_3$, —CONH$_2$, —CONHCH$_3$, —CH(CH$_3$)OH or, more preferably, —C(CH$_3$)$_2$OH Conveniently, in the compounds of general formula (I), the group Het—CH$_2$— is attached at the 5- or 6-position on the benzofuran ring, and especially the 5-position.

Still conveniently, in the compounds of general formula (I), R$^4$ and R$^5$ may each independently represent a hydrogen atom or a halogen atom. In particular R$^4$ and R$^5$ each represent hydrogen atoms.

Particularly preferred compounds of the invention include:

3-[[3-bromo-2-[2-(1H-tetrazol-5-yl)phenyl]-5-benzofuranyl]methyl]-2-ethyl-5,7-dimethyl-3H-imidazo[4,5-b]pyridine;

3-[[3-bromo-2-[2-(1H-tetrazol-5-yl)phenyl]-5-benzofuranyl]methyl]-2-ethyl-5-methyl-3H-imidazo[4,5-b]pyridine;

3-[[3-bromo-2-[2-(1H-tetrazol-5-yl)phenyl]-5-benzofuranyl]methyl]-2-ethyl-7-methyl-3H-imidazo[4,5-b]pyridine-5-carboxylic acid;

3-[[3-bromo-2-[2-(1H-tetrazol-5-yl)phenyl]-5-benzofuranyl]methyl]-5,7-dimethyl-2-propyl-3H-imidazo[4,5-b]pyridine;

3-[[3-bromo-2-[2-(1H-tetrazol-5-yl)phenyl]-5-benzofuranyl]methyl]-7-methyl-2-propyl-3H-imidazo[4,5-b]pyridine-5-carboxylic acid;

3-[[3-bromo-2-[2-(1H-tetrazol-5-yl)phenyl]-5-benzofuranyl]methyl]-2-propyl-3H-imidazo[4,5-b]pyridine-5-carboxylic acid;

3-[[3-bromo-2-[2-(1H-tetrazol-5-yl)phenyl]-5-benzofuranyl]methyl]-2-ethyl-3H-imidazo[4,5-b]pyridine-5-carboxylic acid;

3-[[3-bromo-2-[2-[[(trifluoromethyl)sulphonyl]amino]phenyl]-5-benzofuranyl]-methyl]-2-ethyl-7-methyl-3H-imidazo[4,5-b]pyridine-5-carboxylic acid;

3-[[3-bromo-2-[2-[[(trifluoromethyl)sulphonyl]amino]phenyl]-5-benzofuranyl]methyl]-7-methyl-2-propyl-3H-imidazo[4,5-b]pyridine-5-carboxylic acid;

3-[[3-bromo-2-[2-[[(trifluoromethyl)sulphonyl]amino]phenyl]-5-benzofuranyl]methyl]-2-propyl-3H-imidazo[4,5-b]pyridine-5-carboxylic acid;

3-[[3-bromo-2-[2-[[(trifluoromethyl)sulphonyl]amino]-phenyl]-5-benzofuranyl]methyl]-2-ethyl-3H-imidazo[4,5-b]pyridine-5-carboxylic acid;

3-[[3-bromo-2-[2-[[(trifluoromethyl)sulphonyl]amino]-phenyl]-5-benzofuranyl]methyl]-2-ethyl-N-methyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-N,2-diethyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-2-ethyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-2-ethyl-N,7-dimethyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-N,2-diethyl-7-methyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-2-ethyl-7-methyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-N-methyl-2-propyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-N-ethyl-2-propyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-2-propyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-N,7-dimethyl-2-propyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-N-ethyl-7-methyl-2-propyl-3H-imidazo[4,5-b]pyridine-5-carboxamide;

3-[[3-bromo-2-[2-[[(trifluoromethyl)sulphonyl]amino]-phenyl]-5-benzofuranyl]methyl]-7-methyl-2-propyl-3H-imidazo[4,5-b]pyridine-5-carboxamide;

and physiologically acceptable salts, solvates and metabolically labile esters thereof.

Further preferred compounds of the present invention include:

3-[[3-bromo-2-(2-carboxyphenyl)-5-benzofuranyl]methyl]-2-ethyl-3H-imidazo[4,5-b]pyridine-5-carboxylic acid;

2-[3-bromo-5-[(2-ethyl-7-methyl-3H-imidazo[4,5-b]pyridin-3-yl)methyl]-2-benzofuranyl]benzoic acid;

N-[2-[3-bromo-5-[(2-ethyl-7-methyl-3H-imidazo[4,5-b]pyridin-3-yl)methyl]-2-benzofuranyl]phenyl]-2,2,2-trifluoromethane-sulphonamide;

3-[[3-bromo-2-(2-carboxyphenyl)-5-benzofuranyl]methyl]-2-ethyl-7-methyl-3H-imidazo[4,5-b]pyridine-5-carboxylic acid;

and physiologically acceptable salts, solvates and metabolically labile esters thereof.

Still further preferred compounds of the present invention include:

3-[[3-bromo-2-[2-(1H-tetrazol-5-yl)phenyl]-5-benzofuranyl]methyl]-2-ethyl-3H-imidazo[4,5-b]pyridine-5-methanol;

3-[[3-bromo-2-[2-(1H-tetrazol-5-yl)phenyl]-5-benzofuranyl]methyl]-2-ethyl-7-methyl-3H-imidazo[4,5-b]pyridine-5-methanol;

2-[3-bromo-5-[(2-ethyl-5-hydroxymethyl-3H-imidazo[4,5-b]pyridin-3-yl)methyl]-2-benzofuranyl]-benzoic acid;

2-[3-bromo-5-[(2-ethyl-5-hydroxymethyl-7-methyl-3H-imidazo[4,5-b]pyridin-3-yl)methyl]-2-benzofuranyl]-benzoic acid;

3-[[3-bromo-2-[2-[[(trifluoromethyl)sulphonyl]amino]-phenyl]-5-benzofuranyl]methyl]-2-ethyl-3H-imidazo[4,5-b]pyridine-5-methanol;

3-[[3-bromo-2-[2-[[(trifluoromethyl)sulphonyl]amino]-phenyl]-5-benzofuranyl]methyl]-2-ethyl-7-methyl-3H-imidazo[4,5-b]pyridine-5-methanol;

and physiologically acceptable salts, solvates and metabolically labile esters thereof.

The physiologically acceptable acid addition salts of the compounds of formula (I) may be derived from inorganic or organic acids. Examples of such salts include hydrochlorides, hydrobromides, sulphates, phosphates, benzoates, methanesulphonates or trifluoroacetates.

The compounds may also form salts with suitable bases. Examples of such salts are alkali metal (e.g. sodium or potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, tetraethylammonium, piperidinium, ethylenediammonium and choline).

It will be appreciated that, for pharmaceutical use, the salts referred to above will be physiologically acceptable, but other salts may find use, for example, in the preparation of the compounds of general formula (I) and the physiologically acceptable salts thereof.

It will be further appreciated that the compounds of general formula (I) may be chemically modified in the form of compounds which in vivo (for example, by enzymic attack) will provide the parent compounds of general formula (I). Such prodrugs may be, for example, physiologically acceptable metabolically labile ester derivatives. These may be formed by esterification, for example of any of the carboxylic acid groups in the parent compound of general formula (I), with prior protection of any other reactive groups present in the molecule. Examples of such esters include lower alkyl esters (e.g. methyl or ethyl esters), alkenyl esters (e.g. vinyl or allyl esters), alkynyl esters(e.g. ethynyl or propynyl esters), alkoxyalkyl esters, (e.g. methoxymethyl or 2-methoxyethyl esters), alkylthioalkyl esters (e.g. methylthiomethyl esters) haloalkyl esters (e.g. 2-iodoethyl or 2,2,2-trichloroethyl esters), alkanoyloxyalkyl esters (e.g. acetoxymethyl, 1-acetoxyethyl or pivaloyloxymethyl esters), alkoxycarbonyloxyalkyl esters (e.g. 1-ethoxycarbonyloxyethyl or 1-methoxycarbonyloxyethyl esters), aroyloxyalkyl esters (e.g. benzoyloxymethyl or 1-benzoyloxyethyl esters), substituted or unsubstituted aralkyl esters (e.g. benzyl or 4-amidobenzyl esters), substituted or unsubstituted aminoalkyl esters (e.g. aminoethyl or 2-N,N-dimethylaminoethyl esters) or hydroxyalkyl esters (e.g. 2-hydroxyethyl or 2,3-dihydroxypropyl esters).

In addition to the above ester derivatives the present invention includes within its scope compounds of general formula (I) in the form of other physiologically acceptable equivalents, i.e. physiologically acceptable compounds which, like the metabolically labile esters, are converted in vivo into the parent compounds of general formula (I).

According to a second aspect of the present invention we provide a compound of general formula (I) or a physiologically acceptable salt, solvate or metabolically labile ester thereof for use in therapy.

In particular, the compounds of the present invention may be used in the treatment or prophylaxis of hypertension (for example, essential, malignant or resistant, caused by oral contraceptives, coarctation of the aorta or renal vascular disease) and pulmonary hypertension.

The compounds of the present invention may also be used in the treatment or prophylaxis of congestive heart failure, acute or chronic heart failure, aortic or cardiac insufficiency, post-myocardial infarction, renal insufficiency and renal failure (for example, as a result of diabetic nephropathy, glomerular nephritis, scleroderma or renal crisis), proteinuria, Bartter's syndrome, secondary hyperaldosteronism, Reynaud's syndrome, cerebrovascular insufficiency, peripheral vascular disease, diabetic retinopathy, atherogenesis and for the improvement of vascular compliance.

They are also potentially useful for the treatment of cognitive disorders such as dementia (e.g. Alzheimer's disease) and other CNS disorders, such as anxiety disorders, schizophrenia, depression and alcohol or drug (e.g. cocaine) dependency.

According to a further aspect of the present invention we provide a compound of general formula (I) or a physiologically acceptable salt, solvate or metabolically labile ester thereof for use in the treatment of the aforementioned diseases, especially hypertension.

According to another aspect of the present invention we provide a compound of general formula (I) or a physiologically acceptable salt, solvate or metabolically labile ester thereof for the manufacture of a therapeutic agent for the treatment of the aforementioned diseases, especially hypertension.

According to a further aspect of the present invention we provide a method of treating the aforementioned diseases, especially hypertension, which method comprises administering an effective amount to a patient in need of such treatment of a compound of general formula (I) or a physiologically acceptable salt, solvate or metabolically labile ester thereof.

It will be appreciated that the compounds of general formula (I) or a physiologically acceptable salt, solvate, or metabolically labile ester thereof may advantageously be used in conjunction with one or more other therapeutic agents, such as for example diuretics and/or different antihypertensive agents such as β-blockers, calcium channel blockers or ACE inhibitors. It is to be understood that such combination therapy constitutes a further aspect of the present invention.

It will be further appreciated that reference herein to treatment extends to prophylaxis as well as to the treatment and relief of established symptoms.

While it is possible that a compound of general formula (I) may be administered as the raw chemical it is preferable to present the active ingredient as a pharmaceutical formulation.

The compounds of general formula (I) and their physiologically acceptable salts, solvates and metabolically labile esters may be formulated for administration in any convenient way, and the invention also includes within its scope pharmaceutical compositions comprising at least one compound of general formula (I) or a physiologically acceptable salt, solvate or metabolically labile ester thereof adapted for use in human or veterinary medicine. Such compositions may be presented for use in conventional manner in admixture with one or more physiologically acceptable carriers or excipients. The carrier(s) must be 'acceptable' in the sense of being compatible with the other ingredients of the formulation and not deleterious to the recipient thereof.

Thus, the compounds according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan monooleate; non-aqueous vehicles (which may include edible oils), for example, propylene glycol or ethyl alcohol; and preservatives, for example, methyl or propyl p-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

It will be appreciated that both tablets and capsules may be manufactured in the form of sustained release formulations, such that they provide a controlled continuous release of the compounds according to the invention over a period of hours.

The compounds of general formula (I) and their physiologically acceptable salts, solvates and metabolically labile esters may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, when the compositions comprise dosage units, each unit will preferably contain 5 mg to 500 mg , advantageously where the compounds are to be administered orally 25 mg to 400 mg of the active compound. The daily dosage as employed for adult human treatment will preferably range from 5 mg to 3 g , most preferably from 25 mg to 1 g which may be administered in 1 to 4 daily doses.

The compounds of the invention may be prepared by a number of processes as described below wherein the various groups are as defined for general formula (I) unless otherwise specified.

Thus, according to a further aspect of the present invention we provide a process (A) for preparing the compounds of general formula (I) which comprises treating a compound of general formula (II)

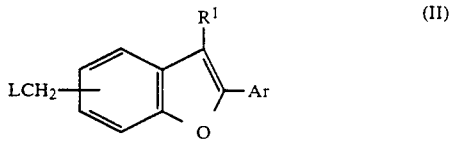

(wherein L is a leaving group, for example a halogen atom such as chlorine, bromine or iodine, or a hydrocarbylsulphonyloxy group such as methanesulphonyloxy, or p-toluenesulphonyloxy and $R^1$ and Ar are as defined in general formula (I)) with an imidazole of formula (III)

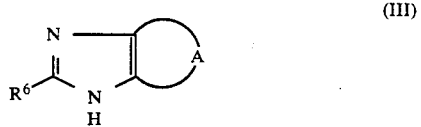

(wherein $R^6$ and A are as defined in general formula (I)) followed by the removal of any protecting groups where present, as described hereinafter.

The reaction is preferably effected under basic conditions, for example, in the presence of sodium hydride, potassium carbonate or sodium methoxide. The reaction is conveniently effected in a solvent such as acetonitrile or an ether e.g. tetrahydrofuran or dioxan, a ketone e.g. butanone or methyl isobutyl ketone, or a substituted amide e.g. dimethylformamide, at a temperature between 0° C. and the reflux temperature of the solvent.

In another general process (B) a compound of general formula (I) may be obtained by deprotection of a protected intermediate of general formula (IV)

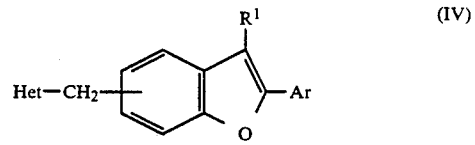

(wherein $R^1$, Ar and Het are as defined in general formula (I) except that at least one reactive group is blocked by a protecting group).

The protecting groups may be any conventional protecting groups, for example as described in "Protective Groups in Organic Synthesis" by Theodora Greene (John Wiley and Sons Inc., 1981). Examples of carboxyl protecting groups include $C_{1-6}$alkyl such as methyl or t-butyl, or $C_{7-10}$aralkyl such as benzyl.

When $R^3$ is a tetrazole group, this may be protected with, for example, the trityl group —C(phenyl)$_3$, or a p-nitrobenzyl or 1-ethoxyethyl group.

Deprotection to yield the compound of general formula (I) may be effected using conventional techniques. Thus, for example, aralkyl groups may be cleaved by hydrogenolysis in a suitable organic solvent such as an alcohol, e.g. ethanol, in the presence of a noble metal catalyst such as palladium or an oxide thereof on a support such as charcoal, and conveniently at room temperature and pressure. Carboxyl protecting groups such as alkyl groups may be cleaved by hydrolysis using a base such as an alkali metal hydroxide (e.g. sodium hydroxide or potassium hydroxide) in a suitable solvent (e.g. an aqueous alcohol such as methanol or ethanol) at any suitable temperature up to reflux. Alternatively, in the case of t-butyl protecting groups, these may be removed by treatment with a strong acid (e.g. trifluoroacetic acid) in a suitable solvent such as dichloromethane. Deprotection of the tetrazole group when protected with a trityl group may be effected by acid hydrolysis using trifluoroacetic acid or a mineral acid such as hydrochloric acid in a suitable solvent such as ethanol conveniently at room temperature. Alternatively, when possible, deprotection of the tetrazolyl group can be effected by catalytic hydrogenation as previously described.

In another general process (C) a compound of general formula (I) in which the substituent $R^3$ in the group Ar represents a C-linked tetrazolyl group may be prepared from a compound of general formula (Ia)

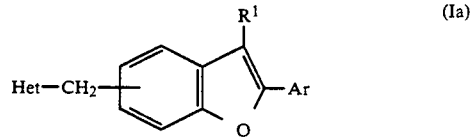

(wherein $R^1$, Ar and Het are as defined in general formula (I) except that in the group Ar, $R^3$ represents a nitrile group and in the group Het, none of $R^{7a}$, $R^{7b}$, $R^{7c}$ and $R^{7d}$ represents a nitrile group) by reaction with a suitable azide such as sodium azide, ammonium azide (preferably prepared in situ from sodium azide and ammonium chloride), trialkyl-(e.g. triethyl) ammonium azide (preferably prepared in situ from sodium azide and a trialkylamine salt (e.g. triethylamine hydrochloride)), a trialkylsilyazide (e.g. trimethylsilylazide) or a tri-alkyl tin azide e.g. tributyl tin azide. The reaction is conveniently effected in a solvent such as xylene, an ether, for example, dimethoxyethane or tetrahydrofuran, or a substituted amide, for example, dimethylformamide at an elevated temperature, such as the reflux temperature of the solvent, for between 1 and 10 days. Where the azide is tributyl tin azide the reaction may conveniently be effected in the absence of a solvent at a temperature between room temperature and 180° C. Such a reaction leaves the tetrazolyl group protected with a tributyl tin group, which can readily be removed using aqueous base or acid. Where aqueous base is used to effect this deprotection, the compound may be treated with an aqueous acid to liberate the free tetrazole.

Compounds of general formula (Ia) may be prepared by processes analogous to those described herein commencing from a compound of formula (IX) and a corresponding benzofuran intermediate.

The intermediate compounds of general formula (Ia) and their acid addition salts are novel compounds and form a further aspect of the present invention.

In another general process (D) a compound of general formula (I) in which the substituent $R^3$ in the group Ar represents $-NHSO_2CF_3$, may also be prepared from a compound of general formula (Ib)

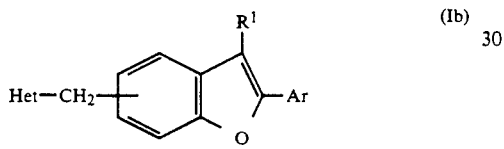

(wherein $R^1$, Ar and Het are as defined in general formula (I) except that in the group Ar, $R^3$ represents an amino group and in the group Het, none of $R^{7a}$, $R^{7b}$, $R^{7c}$ and $R^{7d}$ represents an alcoholic group) by reaction with trifluoromethanesulphonic anhydride or trifluoromethylsulphonyl chloride, in a suitable solvent such as a halogenated hydrocarbon, for example, dichloromethane or chloroform in the presence of a base, e.g. triethylamine.

Compounds of general formula (Ib) may be prepared by processes analogous to those described herein commencing from a compound of formula (X) and a corresponding benzofuran intermediate.

Alternatively, compounds of general formula (Ib) may be prepared by a Curtius rearrangement of a compound of formula (I) wherein $R^3$ in the group Ar is $-CO_2H$ (provided that this is the only unprotected carboxyl group in the molecule) using, for example, diphenylphosphorylazide in the presence of a base such as triethylamine and in a solvent such as an alcohol (e.g. tert-butanol) to form a carbamate followed by deprotection of the amine in a conventional manner, for example by acid hydrolysis using hydrochloric acid in a solvent such as ethanol.

The intermediate compounds of general formula (Ib) and their acid addition salts are novel compounds and form a further aspect of the present invention.

In another general process (E) a compound of general formula (I) may be obtained by treating a compound of formula (Ic)

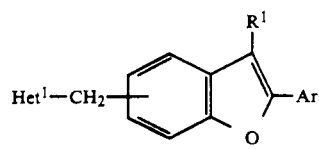

(wherein $R^1$ and Ar are as defined in general formula (I) and $Het^1$ represents the group

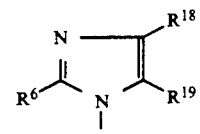

wherein $R^6$ is as defined in general formula (I) and $R^{18}$ and $R^{19}$ represent, respectively, $-CO_2R^{17}$ and $-NH_2$; $-NH_2$ and $-CO_2R^{17}$; $-CONH_2$ and $-NH_2$; $-NH_2$ and $-CONH_2$; or $-CO_2R^{17}$ and $-CO_2R^{17}$) with one of the compounds of formula (V(a)) to (V(d))

$R^{8a}-N=C=O;$ (a)

$R^{8a}-NH-CONH_2;$ (b)

$R^{7a}-C(C_{1-4}alkoxy)_3;$ (c)

$H_2NNH_2$ (d)

(wherein $R^{7a}$ and $R^{8a}$ are as defined in general formula (I)) followed by the removal of any protecting group where present, as described above.

It will be appreciated by a person skilled in the art, that the choice of substituents $R^{18}$ and $R^{19}$ in the compound of formula (Ic) combined with a given structure of formula (V) will enable the synthesis of several of the groups represented by A in general formula (I).

Thus, for example, compounds of general formula (I) wherein Het represents

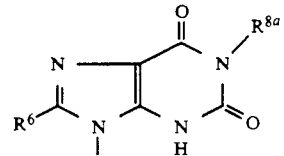

or

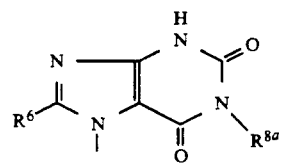

may be prepared by the reaction of a compound of formula (Ic) (wherein $R^{18}$ and $R^{19}$ represent, respectively, $-CO_2R^{17}$ and $-NH_2$; or $-NH_2$ and $-CO_2R^{17}$) with a compound of formula (V(a)), or alternatively (where $R^{18}$ and $R^{19}$ represent, respectively, $-CONH_2$ and $-NH_2$; or $-NH_2$ and $-CONH_2$) with a compound of formula (V(b)) at an elevated temperature.

Compounds of general formula (I) wherein Het represents

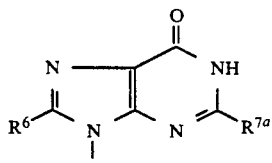

or

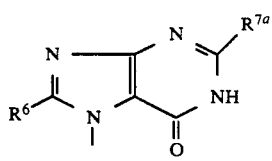

may be prepared by the reaction of a compound of formula (Ic) (wherein $R^{18}$ and $R^{19}$ represent, respectively, —$CONH_2$ and —$NH_2$; or —$NH_2$ and —$CONH_2$) with a compound of formula (V(c)) in the presence of acetic anhydride or dimethylformamide.

Compounds of general formula (I) wherein Het represents

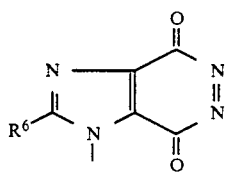

may be prepared by the reaction of a compound of formula (Ic) (wherein $R^{18}$ and $R^{19}$ each represent —$CO_2R^{17}$) with a compound of formula (V(d)) followed by oxidation of the hydrazo intermediate using, for example, NaOBr or 2,3-dichloro-5,6-dicyanoquinone (DDQ).

In the processes (A),(B), (C), (D) and (E) described above, the compounds of general formula (I) may be obtained in the form of a salt, conveniently in the form of a physiologically acceptable salt. Where desired, such salts may be converted into the corresponding free acids or free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

The intermediate compounds of general formula (II) may be prepared from a compound of formula (VI):

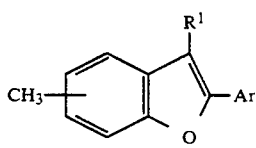

using any suitable reagent well known in the art for converting the methyl on the 6-membered ring into the group —$CH_2L$ (wherein L is as defined above). Thus, for example, when L is a halogen atom, a compound of formula (VI) can be converted into a compound of general formula (II) using N-chloro amides, tert-butyl hypochlorite or N-bromosuccinimide. Halogenation of the side chain may be catalysed by light, thus the reaction can be illuminated with a suitable artificial light source, and preferably in the presence of a free radical initiator such as azobisisobutyronitrile (AIBN) or benzoyl peroxide.

Compounds of formula (VI) wherein $R^1$ is a halogen atom, for example, a bromine atom, may be prepared by halogenation of a compound of formula (VI) wherein $R^1$ represents a hydrogen atom, using for example, bromine, in a suitable solvent such as a halogenated hydrocarbon, e.g. carbon tetrachloride.

Compounds of formula (VI) may be prepared by reaction of a compound of formula (VII)

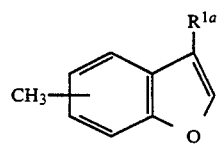

(wherein $R^{1a}$ represents a hydrogen atom or a group selected from $C_{1-6}$alkyl $C_{2-6}$alkenyl or fluoro$C_{1-6}$alkyl) with a compound of formula (VIII)

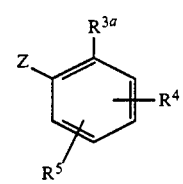

(wherein Z represents a bromine or iodine atom or the group —$OSO_2CF_3$, $R^4$ and $R^5$ are as defined in general formula (I) and $R^{3a}$ is as defined for $R^3$ in general formula (I) or is a protected derivative thereof).

The compound of formula (VII) is first treated with an alkyl lithium compound such as n-butyl lithium at a reduced temperature, for example, between −100° C. and 0° C. in a solvent such as an ether (e.g. tetrahydrofuran). The mixture is then treated with a trialkyl tin halide compound such as triethyl tin chloride to produce a compound of formula (VIIa). Alternatively the lithiated precursor may be treated with a trialkylborate such as triisopropylborate and the temperature conveniently brought up to room temperature. Subsequently, water may be added and the mixture treated with a mineral acid such as sulphuric acid thus producing a compound of formula (VIIA)

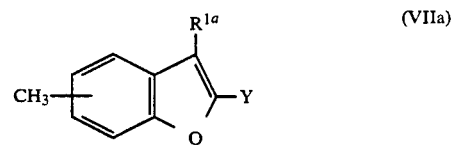

(wherein Y represents a trialkyl tin (e.g. trimethyl tin) or a boronic acid group).

The intermediate compound of formula (VIIa) is then reacted with a compound of formula (VIII) in the presence of a palladium (0) compound such as tetrakis(triphenylphosphine) palladium (0) in a solvent such as an ether (e.g. dimethoxyethane), and in the presence of a base such as sodium carbonate or thallium hydroxide. The reaction is conveniently effected at an elevated temperature, such as the reflux temperature of the solvent.

Compounds of formula (VI) in which the substituent $R^3$ in the group Ar represents a C-linked tetrazolyl group may be prepared from a precursor of a compound of formula (VI) wherein the substituent $R^3$ represents a nitrile group using the reagents and conditions described in process (C).

Similarly, intermediates of formula (VIII) wherein $R^{3a}$ represents a C-linked tetrazolyl group may be prepared from a compound of formula (IX)

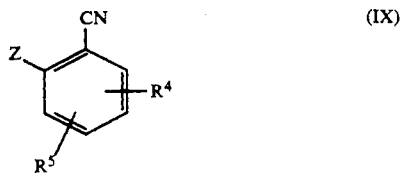

(followed where necessary by protection of any reactive groups), using methods well-known in the art such as those described in process (C).

Compounds of formula (VI) in which the substituent $R^3$ in the group Ar is —NHSO$_2$CF$_3$ may be prepared from a precursor of a compound of formula (VI) wherein the substituent $R^3$ is an amine group using the reagents and conditions described in process (D).

Similarly, intermediates of formula (VIII) wherein $R^{3a}$ represents —NHSO$_2$CF$_3$ may be prepared from a compound of formula (X),

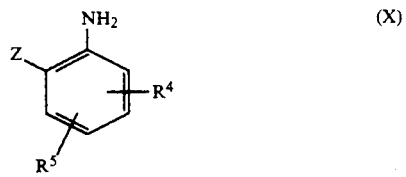

(followed where necessary by the protection of any reactive group) using methods well known in the art such as those described in process (D).

Compounds of formula (VI) may also be prepared by the reaction of a compound of formula (XI)

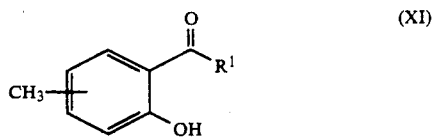

(wherein $R^1$ is as previously defined with the exception of CHO, COR$^2$, where $R^2$ is C$_{1-6}$alkoxy or —NR$^{12}$R$^{13}$, and halogen) with a suitably substituted benzene of formula (XII)

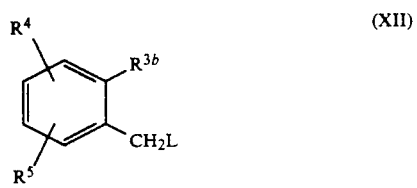

(wherein L is as previously defined and $R^{3b}$ is as defined for $R^{3a}$ in formula (VIII) with the exception of —CO$_2$H and —NHSO$_2$CF$_3$ or is a nitrile group suitable for subsequent conversion into a tetrazolyl group or is a nitro group suitable for conversion into —NHSO$_2$CF$_3$), in the presence of a base such as sodium hydride or potassium carbonate. The formation of the compound of formula (VI) is a two step reaction which requires up to one equivalent of base per step. It will be appreciated however that the reaction can be effected in the presence of two equivalents of base to avoid the need to isolate the intermediate. The reaction is conveniently effected in a solvent such as an ether e.g. tetrahydrofuran, an alcohol e.g. ethanol or a substituted amide e.g. dimethylformamide, at a temperature between room temperature and the reflux temperature of the solvent.

The intermediates of formula (III) are either known compounds or may be made by methods analogous to those used for the preparation of the known compounds (see, for instance, "Comprehensive Heterocyclic Chemistry" Eds. A R Katritzky & C W Rees.)

Compounds of general formula (Ic) may be made by processes analogues to those described herein as process (A).

It will be appreciated that compounds of formula (VI) in which $R^1$ represents a hydrogen or halogen atom may also be converted into compounds of formula (VI) in which $R^1$ represents the group methyl (via hydrogenolysis of the Mannich base), —CHO or —COR$^2$ (wherein $R^2$ is as defined in general formula (I)) using techniques well known in the art, such as those described in "Heterocyclic Chemistry" by J. A. Joule and G. F. Smith, Van Nostrand Reinhold Company, London (1972), "Heterocyclic Chemistry" by A. Albert, 2nd Edition, The Athlone Press, London (1968), "Heterocyclic Compounds", Vol. 29 by A. Mustafa, John Wiley and Sons Inc., New York (1974), "Heterocyclic Compounds", Vol. 2 by R. C. Elderfield, John Wiley and Sons Inc., New York (1951) and "Advances in Heterocyclic Chemistry", Vol. 29 by A. R. Katritsky and A. J. Boulton, Academic Press, New York (1981).

Intermediates of formulae (V), (VI), (VII), (VIII), (IX), (X), (XI) and (XII), are either known compounds or may be prepared by methods analogous to those used for the preparation of the known compounds.

The following examples illustrate the invention. Temperatures are in °C. "Dried" refers to drying using magnesium sulphate. Thin layer chromatography (t.l.c.) was carried out over silica and column chromatography was carried out on silica (Merck 9385 unless otherwise stated), using one of the following solvent systems: A—ether:hexane, B—ether:petroleum ether, C—dichloromethane:ethanol:ammonia, D—dichloromethane:ether, E—ethyl acetate:acetic acid, F—ethyl acetate:hexane, G—dichloromethane:methanol, H—dichloromethane:hexane or I—methanol:ethyl acetate.

The following abbreviations are used: THF—tetrahydrofuran; DME—dimethoxyethane; AIBN—azobisisobutyronitrile; DMF—dimethylformamide; TMEDA—tetramethylethylenediamine; NBS—N-bromosuccinimide; DMAP—4-dimethylaminopyridine; DEAD—diethyl azodicarboxylate.

The following abbreviations are used in the Tables of exemplification:

Me=methyl; Et=ethyl; t-Bu=tert-butyl; Tet=1H-tetrazole; Tet-P=2-(triphenylmethyl)-2H-tetrazole; t-BOC=N-tert-butoxycarbonyl.

Intermediate 1

5-Methylbenzofuran-2-boronic acid n-Butyl lithium (1.7M, 35.16 ml) was added dropwise to a stirred solution of TMEDA (9.58 ml) and 5-methylbenzofuran (8.22 g) in ether (250 ml) maintaining the temperature below $-60°$ C. throughout. The solution was warmed to about $-10°$ C. over 45 minutes and stirred at this temperature for 30 minutes. A precipitate formed on warming. The suspension was cooled and triisopropylborate (43 ml) was added, maintaining the temperature below $-60°$ C. The solution was warmed gradually to room temperature before quenching with 2N HCl (70 ml). The mixture was extracted with ether ($3\times50$ ml) and the combined organic extracts washed with 2N HCl ($4\times30$ ml), water ($2\times30$ ml) and dried before evaporation to give the title compound as an orange solid (12.75 g).

T.l.c. System A (1:1), Rf 0.3.

Intermediate 2

2-(5-Methyl-2-benzofuranyl)benzonitrile

Intermediate 1 (20 g) was added to a stirred solution of 2-bromobenzonitrile (10.34 g) and tetrakis(triphenylphosphine)palladium (0) (1.5 g) in DME (200 ml) and 8% NaHCO$_3$ (50 ml) at reflux under nitrogen. Further catalyst (1.5 g) was added and the reaction continued overnight. The reaction was cooled to room temperature and diluted with ether (200 ml). The organic layer was separated, washed with water ($3\times100$ ml) and dried. Filtration and evaporation gave a white solid which was purified by chromatography eluting with System A (1:9) to give the title compound (10.58 g) as a white solid. T.l.c. System A (1:9), Rf 0.45.

Intermediate 2 was also prepared by the alternative two-step reaction:

a) 2-Hydroxy-5-methylbenzaldehyde p-Cresol (100 g) in dry THF(100 ml) was added dropwise to a mechanically stirred, freshly prepared solution of ethyl magnesium bromide [magnesium (25.0 g) and bromoethane (75 ml)] in THF (500 ml) under nitrogen at a rate which maintained a slow reflux (about 30 mins). After 30 mins toluene (1.21) was added, followed by 1,3-dimethyl-3,4,5,6-tetrahydro-2(1H)-pyrimidone (125 ml), and paraformaldehyde (70 g). The mixture was then heated at reflux for 16 h. The mixture was concentrated by distillation and aqueous hydrochloric acid (2M, 600 ml) then added. Water (600 ml) was added and the mixture filtered through "hyflo". The organic phase was separated, dried, filtered and concentrated in vacuo to give a brown oil. The oil was steam distilled and the product extracted from the distillate with ether (1 liter). The organic extract was dried, filtered and concentrated in vacuo to give a pale yellow slurry which was cooled to $-10°$ C., triturated with ether (precooled to $-78°$ C., 100 ml), filtered off rapidly and washed with ether (precooled to $-78°$ C.) to give the title compound as colourless needles, (131.4 g).

T.l.c. System A (1:5) Rf 0.5.

b) 2-(5-Methyl-2-benzofuranyl)benzonitrile

A solution of the product of step (a) (130 g) in dry DMF (400 ml) was added dropwise to a solution of sodium methoxide (56.2 g) in ethanol (400 ml) mechanically stirred under nitrogen. After 20 mins, a solution of 2-(bromomethyl)benzonitrile (182.2 g) in dry DMF (400 ml) was added dropwise. The mixture was then heated to 75° C. for 30 min. The solution was allowed to cool for 1 h. A slurry of sodium methoxide (56.2 g) in dry DMF (100 ml) was added and the mixture heated at reflux for 1.5 h. The mixture was concentrated in vacuo and then poured into iced water. The solid was collected, and then triturated with methanol to give the title compound (Intermediate 2) as a beige solid (149.4 g).

T.l.c. System A (1:9) Rf 0.4.

Intermediate 3

5-[2-(5-Methyl-2-benzofuranyl)phenyl]-1H-tetrazole

A suspension of Intermediate 2 (94 g) in tri-n-butyl tin azide (268 g) was heated at 100°–125° C. for 1.25 h under nitrogen. The resulting solution was then heated at 155°–160° C. for 2 h under nitrogen, then poured into a solution of aqueous sodium hydroxide (0.8N, 3070 ml). This solution was extracted with ether. The aqueous phase was acidified to pH1 with 5N hydrochloric acid and the resulting precipitate filtered, washed with water and dried under vacuum. The solid was dissolved in ethyl acetate, washed with brine and dried. The solvent was evaporated to give the title compound as a buff-coloured solid (100.3 g).

T.l.c. System A (1:1), Rf 0.2.

Intermediate 4

5-[2-(3-Bromo-5-methyl-2-benzofuranyl)phenyl]-1H-tetrazole

A solution of bromine (58 g), in carbon tetrachloride (140 ml) was added dropwise over 35 min to a mechanically stirred solution of Intermediate 3 (50 g) in dry dioxan (2090 ml) at room temperature under nitrogen. The resulting solution was stirred at room temperature for 3h, then cyclohexene (63 ml) was added. Another preparation of the product was carried out simultaneously on the same scale as described above, and at this stage they were combined. The solvent was evaporated and the residual brown oil (260 g) partitioned between ether and aqueous sodium hydroxide. The alkaline solution was acidified to pH1 with hydrochloric acid, then extracted with ethyl acetate. The combined ethyl acetate extracts were washed with brine, dried and evaporated to give a buff solid (125 g) which was triturated with hot toluene, cooled and filtered off to give the title compound as a cream coloured solid (101.8 g).

T.l.c. Ether/petroleum ether/acetic acid (50:50:1), Rf 0.27.

Intermediate 5

5-[2-(3-Bromo-5-methyl-2-benzofuranyl)phenyl]-2-(triphenylmethyl)-2H-tetrazole Triethylamine (57.4 g) was added to a mechanically stirred suspension of Intermediate 4 (101 g) in dry dichloromethane (2.9 liters) at room temperature under nitrogen. Triphenylmethyl chloride (79.3 g) followed by DMAP (1.0 g) were added at room temperature and the mixture stirred for 3 h under nitrogen. The reaction mixture was washed with water, then brine and dried. The mixture was filtered and concentrated to a volume of about 1.2 liters then loaded onto a column of silica (Merck 9385, 14 cm diam. column). Elution with dichloromethane gave a colourless solid (158.4 g) which was triturated with ether and filtered to give the title compound as a colourless solid (147.9 g).

T.l.c. System H (1:1), Rf 0.28,

Intermediate 6

5-[2-[3-Bromo-5-(bromomethyl)-2-benzofuranyl]-phenyl]-2-(triphenylmethyl)-2H-tetrazole Intermediate 5 (74 g) was dissolved in carbon tetrachloride (2050 ml) by heating the suspension to reflux. The resulting colourless solution was allowed to cool to 50° C. then NBS (22.1 g) was added, followed by benzoyl peroxide (1.1 g). The reaction mixture was heated at reflux for 3.25 h, under nitrogen, then allowed to cool to room temperature. The reaction mixture was washed with water then brine. Another preparation of the product was carried out simultaneously on the same scale as described above, and at this stage they were combined and dried. The solvent was evaporated to give a colourless solid (168 g) which was triturated with ether/methanol (1:1) and filtered to give the title compound as a colourless solid (160.8 g).

T.l.c. System H (1:1), Rf 0.15.

Intermediate 7

1-[[3-Bromo-2-[2-[2-(triphenylmethyl)-2H-tetrazol-5-yl]phenyl]-5-benzofuranyl]methyl]-2-butyl-1H-benzimidazole A solution of 2-butyl-1H-benzimidazole (630 mg) in DMF (50 ml) was treated with sodium methoxide (0.2 g) and the mixture stirred for 0.5 h. Intermediate 6 (2 g) was added and the solution stirred at 20° C. overnight and at 60° C. for 5 h. Further Intermediate 6 (0.5 g) was added and the solution stirred at 60° C. for 2 h. The solution was cooled, then poured into water (300 ml). The solid was filtered off, washed with water and dissolved in ether. Evaporation of the dried solvent gave a white foam (2 g) which was purified by column chromatography eluting with ether to give the title compound as a white foam (1 g).

T.l.c. ether Rf 0.6.

Intermediate 8

N-(5-Amino-4-pyrimidinyl)pentanamide

A mixture of 4,5-diaminopyrimidine (2.77 g) and valeric anhydride (18.84 g) were refluxed under nitrogen for 4 h. The mixture was poured into 2N sodium hydroxide solution (200 ml) and this was stirred at 20° C. overnight. The mixture was extracted with ethyl acetate (8×200 ml) and the combined extracts were dried and concentrated in vacuo to give a white solid (3.74 g). This was triturated with cold ethyl acetate to give the title compound as a white solid (3.53 g).

T.l.c. System C (50:8:1) Rf 0.46.

Intermediate 9

8-Butyl-7H-purine

Intermediate 8 (1.17 g,) was heated at 220° C. in diphenyl ether (15 ml) under nitrogen overnight. The black solution was cooled and diluted with petrol (200 ml) and the precipitate was filtered and dried to give the title compound as a pale brown solid. (747 mg)

T.l.c. System C (50:8:1) Rf 0.56.

Intermediate 10

7-[[3-Bromo-2-[2-[2-(triphenylmethyl)-2H-tetrazol-5-yl]phenyl]-5-benzofuranyl]methyl]-8-butyl-7H-purine Sodium methoxide (230 mg,) was added to a stirred solution of Intermediate 9 (500 mg), in dry DMF (10 ml) under nitrogen. The mixture was allowed to stir for 30 min and then Intermediate 6 (2.63 g) was added, and stirring continued at room temperature overnight. A further quantity of DMF (100 ml) was added and stirring continued for 24 h. The reaction mixture was poured into water (100 ml) and brine (100 ml) and extracted with ethyl acetate (2×300 ml). The organic extracts were combined, washed with water (100 ml) and brine (100 ml), dried and concentrated in vacuo to give a brown oil (3.750 g.) This was purified by short path chromatography to give the title compound as a cream coloured solid (74 mg).

T.l.c. System G (15:1) Rf 0.51,

Intermediate 11

6-Chloro-2,3-pyridinediamine

A solution of tin (II) chloride (21.8 g) in concentrated hydrochloric acid (30 ml) was added, with cooling, to 6-chloro-3-amino-2-nitropyridine (5 g) and the suspension stirred for 3 hours at room temperature. The pH was adjusted to pH12 (40% NaOH) and the solvent removed in vacuo. The residue was purified by flash column chromatography, eluting with System C (100:8:1), to afford the title compound as a yellow solid (3.29 g).

T.l.c. System C (100:8:1) Rf=0.21.

Intermediate 12

5-Chloro-2-ethyl-1H-imidazo[4,5-b]pyridine

A mixture of Intermediate 11 (14 g), propionic acid (0.95 ml) and polyphosphoric acid (350 g) was stirred at 130° C. for 18 hours. After leaving to cool the pH was adjusted to pH9 (NH4OH) and the resulting suspension was filtered. The filter cake was washed with water (800 ml), dichloromethane (300 ml) and ether (300 ml) leaving the title compound as a fawn solid (16.1 g).

T.l.c. Ethyl acetate Rf=0.33.

Similarly prepared was:

Intermediate 13

5-Chloro-2-cyclopropyl-1H-imidazo[4,5-b]pyridine

T.l.c. ethyl acetate Rf=0.50.

From a mixture of Intermediate 11 and cyclopropylformate.

Intermediate 14

5-Bromo-2-ethyl-1H-imidazo[4,5-b]pyridine

A mixture of Intermediate 12 (3.2 g) and hydrogen bromide 30% in acetic acid (20 ml) was stirred under nitrogen at 100° C. for 19 hours. A further portion of hydrogen bromide 30% in acetic acid (30 ml) was added and stirring at 100° C. continued for a further 16 hours. The reaction mixture was poured on to ice (200 ml), neutralized (NH4OH) and extracted into ethyl acetate (5×100 ml). The organic fractions were combined, dried and the solvent removed in vacuo to yield the title compound as a fawn solid (3.6 g).

T.l.c. ethyl acetate Rf=0.32.

Intermediate 15

3-[[3-Bromo-2-[2-[2-(triphenylmethyl)-2H-tetrazol-5-yl]phenyl]-5-benzofuranyl]methyl]-5-chloro-2-ethyl-3H-imidazo[4,5-b]pyridine A solution of Intermediate 12 (150 mg) in DMF (5 ml) was added to a stirred suspension of sodium hydride (40 mg) in DMF (3 ml). The mixture was stirred at room temperature for 20 minutes then cooled and Intermediate 6 (660 mg) was added and the reaction stirred for 18 hours. Water (1 ml) was added and the mixture was concentrated in vacuo. The residue was partitioned between ethyl acetate (30 ml) and brine (40 ml) and the aqueous layer washed with ethyl acetate (3×20 ml). The combined organics were dried and the solvent removed in vacuo. The residue was purified by flash column chromatography eluting with system F (2:1) to yield the title compound as a colourless solid (280 mg).

T.l.c. System F (2:1) Rf=0.47.

Similarly prepared were:

Intermediate 16

3-[[3-Bromo-2-[2-[2-(triphenylmethyl)-2H-tetrazol-5-yl]phenyl]-5-benzofuranyl]methyl]-5-chloro-2-cyclopropyl-3H-imidazo[4,5-b]pyridine T.l.c. ether:hexane:dichloromethane (2:2:1) Rf=0.23.

From Intermediate 13 and Intermediate 6.

Intermediate 17

5-Bromo-3-[[3-bromo-2-[2-[2-(triphenylmethyl)-2H-tetrazol-5-yl]phenyl]-5-benzofuranyl]methyl]-2-ethyl-3H-imidazo[4,5-b]pyridine T.l.c. System F (1:1) Rf=0.43.

From Intermediate 14 and Intermediate 6.

Intermediate 18

5-Bromo-1-[[3-bromo-2-[2-[2-(triphenylmethyl)-2H-tetrazol-5-yl]phenyl]-5-benzofuranyl]methyl]-2-ethyl-1H-imidazo[4,5-b]pyridine m.p. 170°-174° C.

From Intermediate 6 and Intermediate 14.

Intermediate 19

2-Ethyl-3H-imidazo[4,5-b]pyridine-5-carbonitrile

Copper cyanide (2.035 g) was added to a solution of Intermediate 14 (5.0 g) in N-methylpyrrolidinone (70 ml) and the resulting mixture stirred under nitrogen at 200° C. for 5 hour. The mixture was cooled and poured into 35% aqueous ammonia (200 ml) and ethyl acetate (200 ml) and the resulting two phase mixture vigorously stirred for 30 min. The organic phase was removed and the aqueous phase further extracted with ethyl acetate (5×100 ml). The combined organic extracts were washed with saturated brine (100 ml), dried and concentrated to give the crude product (1.0 g). Flash column chromatography eluting with System C (98:2:1) gave the title compound as a yellow solid (400 mg).

T.l.c. System C (96:4:0.5) Rf=0.27.

Intermediate 20

3-[[3-Bromo-2-[2-[2-(triphenylmethyl)-2H-tetrazol-5-yl]phenyl]-5-benzofuranyl]methyl]-2-ethyl-3H-imidazo[4,5-b]pyridine-5-carbonitrile From Intermediate 6 and Intermediate 19 according to the method of Intermediate 15.

T.l.c. System F (1:1) Rf=0.30.

Intermediate 21

3-[[3-Bromo-2-[2-[2-(triphenylmethyl)-2H-tetrazol-5-yl]phenyl]-5-benzofuranyl]methyl]-2-ethyl-N-methyl-3H-imidazo[4,5-b]pyridine-5-carboxamide A mixture of potassium hydroxide (40 mg) and Intermediate 20 (0.1 g) in tert-butanol (8 ml) was heated under reflux for 30 mins. The resulting solution was cooled, and iodomethane (0.04 ml) was added. The mixture was again heated under reflux for 4 h, cooled, and water (40 ml) added. The mixture was extracted with dichloromethane (3×40 ml) and the combined organic extracts dried, filtered and evaporated to give the title compound (80 mg).

T.l.c. System C (96:4:5) Rf=0.3.

Intermediate 22

3-[[3-Bromo-2-[2-[2-(triphenylmethyl)-2H-tetrazol-5-yl]phenyl]-5-benzofuranyl]methyl]-5,7-dimethyl-2-ethyl-3H-imidazo[4,5-b]pyridine From Intermediate 6 and 5,7-dimethyl-2-ethyl-3H-imidazo[4,5-b]pyridine (described in European Patent Specification No. 0 400 974, published 5th Dec. 1990) according to the method of Intermediate 15.

T.l.c. System F (1:1) Rf=0.30.

Intermediate 23

1,1-Dimethylethyl 2-(3-bromo-5-methyl-2-benzofuranyl)benzoate

A mixture of 2-(3-bromo-5-methyl-2-benzofuranyl)-benzoic acid (described in EP-A-0434249) (2.0 g), p-toluenesulphonyl chloride (2.5 g), tert-butanol (10 ml) and pyridine (3 ml) was stirred at 0° C. and allowed to warm to room temperature. Stirring was continued for 72 hours. The mixture was then diluted with ether (100 ml) and washed with 2M hydrochloric acid (75 ml) followed by an aqueous solution of 1M sodium bicarbonate (75 ml). The aqueous solutions were further extracted with ethyl acetate (100 ml) and the combined organic extracts were dried and evaporated in vacuo. Purification by flash column chromatography eluting with dichloromethane:hexane (3:7) gave the title compound (0.6 g) as a colourless gum.

T.l.c. System H (1:2) Rf=0.3.

Intermediate 24

1,1-Dimethylethyl 2-[3-bromo-5-(bromomethyl)-2-benzofuranyl]benzoate

From Intermediate 23 according to the method of Intermediate 6.

T.l.c. System A (1:10) Rf=0.4.

Intermediate 25

1,1-Dimethylethyl 2-[3-bromo-5-[(5,7-dimethyl-2-ethyl-3H-imidazo[4,5-b]pyridin-3-yl)methyl]-2-benzofuranyl]benzoate From Intermediate 24 and 5,7-dimethyl-2-ethyl-3H-imidazo[4,5-b]pyridine (described in EP-A-0400974) according to the method of Intermediate 15.

T.l.c. ethyl acetate:petroleum ether (1:1) Rf=0.55.

Intermediate 26

1,1-Dimethylethyl [2-[3-bromo-5-[(5,7-dimethyl-2-ethyl-3H-imidazo[4,5-b]pyridin-3-yl)methyl]-2-benzofuranyl]phenyl]carbamate Sodium hydride (0.2 g) was added in portions over 5 min to a mixture of 5,7-dimethyl-2-ethyl-3H-imidazo[4,5-b]pyridine (described in EP-A-0400974) (1.0 g) in dry DMF (25 ml) and stirred at room temperature under nitrogen. After 30 min the solution was cooled to 0°-5° C. and 1,1-dimethylethyl [2-[3-bromo-5-(bromomethyl)-2-benzofuranyl]phenyl]carbamate (described in European Patent Specification No. 0 434 249

A, published 26th Jun. 1991) (3.45 g) was added portionwise over 5 min. The mixture was allowed to warm to room temperature and was stirred for 18 h. Water (1 ml) was added and the mixture concentrated in vacuo. Dichloromethane (50 ml) was added and the mixture washed with water (100 ml), dried and concentrated in vacuo. The residue was purified by flash column chromatogrpahy eluting with System D (10:1) to give the title compound (2.0 g) as a colourless foam.

T.l.c. System D (10:2) Rf=0.3.

Intermediate 27

3-[[3-Bromo-2-[2-[2-(triphenylmethyl)-2H-tetrazol-5-yl]phenyl]-5-benzofuranyl]methyl]-2-ethyl-3H-imidazo[4,5-b]pyridine-5-carboxamide A mixture of Intermediate 20 (250 mg), lert-butanol (20 ml) and potassium hydroxide (100 mg) was stirred at reflux, under nitrogen for 40 min. After cooling, water (60 ml) was added and the mixture extracted with dichloromethane (3×60 ml). The organic extracts were dried and concentrated in vacuo to afford the title compound as a white solid (150 mg).

T.l.c. System C (96:4:0.5) Rf=0.33.

Intermediate 28

5-Bromo-2-ethyl-3-(4-methoxyphenyl)methyl-3H-imidazo[4,5-b]pyridine and
5-Bromo-2-ethyl-1-(4-methoxyphenyl)methyl-1H-imidazo[4,5-b]pyridine 60% Sodium hydride (2.5 g) was added to a stirred solution of 5-bromo-2-ethyl-3H-imidazo[4,5-b]pyridine (11.2 g) in anhydrous DHF (150 ml). Stirring was maintained for 30 min after effervesence ceased before addition of p-methoxybenzyl chloride (7.5 ml) and stirring the mixture overnight. Water (200 ml) was added and the mixture extracted with ethyl acetate (3×100 ml) and saturated brine (100 ml), dried and concentrated in vacuo to afford a brown solid. Trituration with System A (1:3) (100 ml) gave a mixture of the title compound (regioisomers) as a light brown solid (15.3 g).

T.l.c. ether Rf=0.33 and 0.12.

Intermediate 29

Methyl 2-ethyl-3-(4-methoxy-3H-imidazo[4,5-b]pyridine-5-carboxylate

A solution of the regioisomers of Intermediate 28 (15.3 g) in anhydrous DMF (160 ml) and methanol (120 ml) was thoroughly purged with nitrogen and triethylamine (14.4 ml), palladium diacetate (3.2 g) and bis(diphenylphosphino)propane (5.75 g) added. The apparatus was purged (×4) with carbon monoxide and heated overnight at 85° C. under a positive pressure of carbon monoxide. The mixture was cooled and water (500 ml) added. The resulting mixture was extracted with ethyl acetate (4×250 ml) and the combined extracts were washed with water (3×250 ml) and saturated brine (250 ml), dried and concentrated in vacuo to give a brown tar. Flash column chromatography afforded the title compound, a single regioisomer, as a brown oil which crystallised to afford a light brown powder (11.1 g).

T.l.c. ethyl acetate Rf=0.47.

Intermediate 30

Methyl 2-ethyl-3H-imidazo[4,5-b]pyridine-5-carboxylate

A mixture of Intermediate 29 (11.0 g) in trifluoroacetic acid (30 ml) was heated at reflux for 36 h before evaporating to dryness. 8% w/v Aqueous sodium hydrogen carbonate (280 ml) was added and the mixture extracted with ethyl acetate (4×500 ml). The combined extracts were washed with saturated brine (500 ml), dried, silica gel (Merck 9385, 50 g) added and the mixture concentrated in vacuo. Flash column chromatography eluting with, 10% ethanol in ether, gave the title compound as a white powder (4.2 g).

T.l.c. ethyl acetate Rf=0.15.

Intermediate 31

Ethyl 2-ethyl-7-methyl-3H-imidazo[4,5-b]pyridine-5-carboxylate

Hydrogen peroxide (30% w/w in water; 14 ml) was added dropwise to stirred and cooled (−10° C.) ethyl pyruvate (22 ml). This mixture and a solution of iron (II) sulphate heptahydrate (37.5 g) in water (45 ml) were added simultaneously, dropwise into a stirred and cooled (−10° C.) solution of 2-ethyl-7-methyl-3H-imidazo[4,5-b]pyridine (7.1 g) in water (23 ml) and concentrated sulphuric acid (7.5 ml). The mixture was then poured onto ice and trisodium citrate dihydrate (40 g) was added. The mixture was neutralised with solid sodium bicarbonate and partitioned between chloroform (×3) and water. The organic phases were combined, dried and evaporated. Column chromatography eluting with 10% methanol in ether gave a brown solid which was triturated with ether to give the title compound as a pale yellow solid (1.9 g), m.p. 151°–153° C.

Intermediate 32

Methyl 3-[[3-bromo-2-[2-(1,1-dimethylethoxy)carbonylphenyl]-5-benzofuranyl]methyl]-2-ethyl-3H-imidazo[4,5-b]pyridine-5-carboxylate A mixture of Intermediate 30 (210 mg) and potassium carbonate (250 mg) in anhydrous DMF (25 ml) were stirred at room temperature for 30 min before Intermediate 24 (0.70 g) was added and the mixture stirred at room temperature for 24 h. Water (100 ml) was added and the mixture extracted with ethyl acetate (3×100 ml). The combined extracts were washed with water (3×100 ml), saturated brine (100 ml), dried and concentrated in vacuo to give a brown oil (900 mg). Flash column chromatography eluting with System F (2:1) gave the title compound as a white powder (300 mg).

T.l.c. System F (2:1) Rf=0.41.

Intermediates 33 to 37 in Table 1 were prepared according to the method of Intermediate 32 (Equation 1):

Equation 1

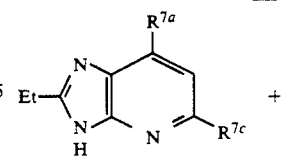

+

-continued
Equation 1

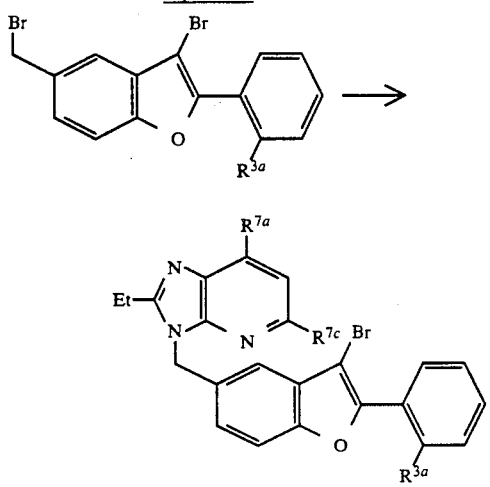

Intermediate 38

3-[[3-Bromo-2-[2-[(1,1-dimethylethoxy)carbonyl]-phenyl]-5-benzofuranyl]methyl]-2-ethyl-3H-imidazo[4,5-b]pyridine-5-carboxylic acid A mixture of potassium hydroxide (150 mg), Intermediate 32 (300 mg), THF (10 ml) and water (4 ml) was rapidly stirred overnight at room temperature. Saturated aqueous ammonium chloride (50 ml) was added and the mixture extracted with ethyl acetate (3×50 ml). The combined extracts were dried and concentrated in vacuo to give the title compound as a fine white powder (280 mg).

n.m.r.(CDCl$_3$) $\delta$1.27 (s,9H), 1.43 (t,3H), 2.92 (q,2H), 5.65 (s,2H), 7.11 (dd,1H), 7.35-7.77 (m,5H), 7.94 (dd,1H), 8.21, 8.26 (AB,2H), Similarly prepared was:

Intermediate 39

3-[[3-Bromo-2-[2-[(1,1-dimethylethoxy)carbonyl]-phenyl]-5-benzofuranyl]methyl]-2-ethyl-7-methyl-3H-imidazo[4,5-b]pyridine-5-carboxylic acid T.l.c. System G (10:1) Rf=0.4.

From a mixture of Intermediate 36 and potassium hydroxide.

Intermediate 40

Methyl 3-[[3-bromo-2-(2-aminophenyl)-5-benzofuranyl]methyl]-2-ethyl-3H-imidazo[4,5-b]pyridine-5-carboxylate Intermediate 33 (348 mg) was treated with trifluoroacetic acid (1 ml) in dichloromethane (4 ml) with stirring at room temperature overnight. Evaporation gave a brown gum which was partitioned between dichloromethane and sodium bicarbonate solution (8%). The combined organic phases were washed with brine and dried. Evaporation gave the title compound as a colourless glass (280 mg).

T.l.c. methanol:ether (1:9) Rf 0.50.

Similarly prepared was:

Intermediate 41

Ethyl 3-[[2-(2-aminophenyl)-3-bromo-5-benzofuranyl]methyl]-2-ethyl-7-methyl-3H-imidazo[4,5-b]pyridine-5-carboxylate T.l.c. ether Rf=0.30.

From a mixture of Intermediate 35 and trifluoroacetic acid.

Intermediates 42 and 43 were prepared according to the method of Intermediate 15:

Intermediate 42

1,1-Dimethylethyl 2-[3-bromo-5-[(2-ethyl-7-methyl-3H-imidazo[4,5-b]pyridin-3-yl)methyl]-2-benzofuranyl]benzoate T.l.c. System G (20:1) Rf=0.3.

From a mixture of Intermediate 24 and 2-ethyl-7-methyl-3H-imidazo[4,5-b]pyridine (described in EP-A-0400974) in the presence of sodium hydride.

Intermediate 43

3-[[3-Bromo-2-[2-[2-(triphenylmethyl)-2H-tetrazol-5-yl]phenyl]-5-benzofuranyl]methyl]-2-ethyl-7-methyl-3H-imidazo[4,5-b]pyridine T.l.c. System G (16:1) Rf=0.81.

From a mixture of Intermediate 6 and 2-ethyl-7-methyl-3H-imidazo[4,5-b]pyridine (described in EP-A-0400974) in the presence of sodium hydride.

Intermediate 44

3-[[3-Bromo-2-[2-[2-(triphenylmethyl)-2H-tetrazol-5-yl]phenyl]-5-benzofuranyl]methyl]-2-ethyl-7-methyl-3H-imidazo[4,5-b]pyridine-5-methanol A mixture of Intermediate 34 (200 mg), sodium borohydride (30 mg), t-butanol (5 ml) and THF (5 ml) was heated at reflux for 8 h. A solution of methanol (0.5 ml) in t-butanol (2 ml) was added dropwise (whilst the reaction was still at reflux) and the mixture then cooled and poured into water (50 ml). The mixture was extracted with ethyl acetate (3×50 ml) and the combined extracts washed with saturated brine (100 ml), dried and concentrated in vacuo to give a foam. Flash column chromatography eluting with dichloromethane:ethanol (40:1) gave the title compound as a colourless oil (110 mg).

T.l.c. ether Rf=0.15.

Intermediate 45 to 47 in Table 2 were prepared according to the method of Intermediate 44 (Equation 2):

Equation 2

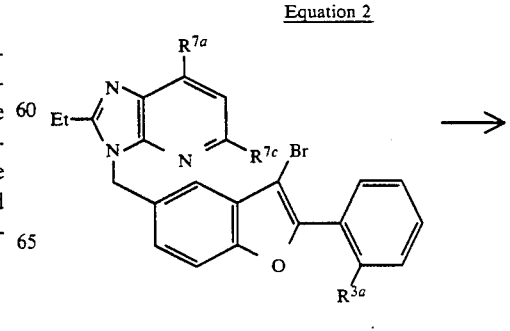

-continued
Equation 2

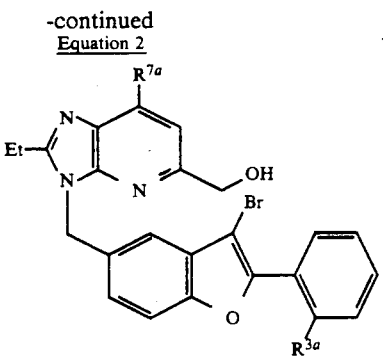

Intermediate 48

1,1-Dimethylethyl 2-[3-bromo-5-[(5-aminocarbonyl-2-ethyl-3H-imidazo[4,5-b]pyridin-3-yl)methyl]-2-benzofuranyl]benzoate N,N'-Carbonyldiimidazole (93 mg) was added to a stirred solution of Intermediate 38 (110 mg) in anhydrous THF (10 ml). The mixture was stirred under nitrogen at room temperature for 3 h before saturated ammoniacal THF (5 ml) was added and the resulting solution allowed to stand overnight at room temperature. The mixture was evaporated to dryness to give a white wax. Flash column chromatography eluting with System G (19:1) afforded the title compound as a white powder (25 mg).

T.l.c. System G (19:1) Rf=0.34.

Similarly prepared was:

Intermediate 49

1,1-Dimethylethyl 2-[3-bromo-5-[(5-aminocarbonyl-2-ethyl-7-methyl-3H-imidazo[4,5-b]pyridin-3-yl)methyl]-2-benzofuranyl]benzoate T.l.c. System G (10:1) Rf =0.65.

From a mixture of N,N-carbonyldiimidazole and Intermediate 39 in anhydrous THF.

Intermediate 50

1-[3-[[3-Bromo-2-[2-[2-(triphenylmethyl)-2H-tetrazol-5-yl]phenyl]-5-benzofuranyl]methyl]-2-ethyl-7-methyl-3H-imidazo[4,5-b]pyridin-5-yl]-1-methyl-ethanol Intermediate 34 (44 mg) in dry THF (2 ml) was cooled under nitrogen to 0° C. Methyl magnesium bromide solution (1.5M in dry toluene-THF 75:25; 100 μl) was added and the mixture was allowed to come to room temperature. After heating to 50° C. for 3 h more of the same methyl magnesium bromide solution (50 μl) was added and heating continued for 2 h. After cooling the mixture was quenched with saturated ammonium chloride solution and partitioned between ethyl acetate (x3) and water. The combined organic layers were washed with brine, dried and purified by column chromatography eluting with ether to give the title nd (25 mg) as a colourless glass.

T.l.c. ether Rf=0.22.

Intermediate 51

Trimethyl (5-methyl-2-benzofuranyl)stannane n-Butyl lithium (1.57M in hexane, 75 ml) was added dropwise to a stirred solution of 5-methylbenzofuran (14 g) in dry THF (150 ml) at −70° under nitrogen over 45 min. The solution was then allowed to warm to −55° before a solution of trimethyltin chloride (23 g) in THF (70 ml) was added dropwise. The solution temperature rose to −32°. The cooling bath was removed and the solution was stirred at room temperature for 2 h. The solution was diluted with ethyl acetate (250 ml) and washed with water (200 ml). The organic layer was dried and concentrated in vacuo to afford a yellow liquid (32 g). Kugelrohr distillation of this liquid gave the title compound (23.3 g) as a colourless liquid, b.p. 115° at 7 mbar.

Intermediate 52

Methyl 2-fluoro-6-iodobenzoate

Concentrated sulphuric acid (0.5 ml) was added to a solution of 2-fluoro-6-iodobenzoic acid (1.03 g) in methanol (35 ml). After stirring at reflux for 5 days, with two further amounts of conc. sulphuric acid (1 ml) being added after 1 and 2 days, the solution was allowed to cool. The reaction mixture was diluted with ethyl acetate (200 ml) before being washed with water (2×80 ml), 8% aqueous sodium bicarbonate (2×100 ml), dried and concentrated in vacuo. Purification by chromatography eluting with System A (1:3) afforded the title compound (0.72 g) as an orange oil.

T.l.c. System A (1:1) Rf 0.6.

Intermediate 53

Methyl 2-fluoro-6-(5-methyl-2-benzofuranyl)benzoate

Tetrakis(triphenylphosphine)palladium (0) (0.19 g) was added to a stirred solution of Intermediate 51 (1.2 g) and Intermediate 52 (0.95 g) in toluene (30 ml). The solution was then stirred at reflux for 3 h before being cooled, diluted with ethyl acetate (35 ml), washed with water (1×50 ml), dried and concentrated in vacuo to afford a red oil (1.7 g). Purification by chromatography (Merck 7734) eluting with System A (1:9) afforded the title compound (0.83 g) as a yellow oil.

Assay Found: C,71.9; H,4.35; $C_{17}H_{13}FO_3$ requires: C,71.8; H,4.6;.

Intermediate 54

Methyl 2-(3-bromo-5-methyl-2-benzofuranyl)-6-fluorobenzoate

From Intermediate 53 according to the method of Intermediate 4.

T.l.c. System A (1:3) Rf=0.5.

Intermediate 55

Methyl 2-[3-bromo-5-(bromomethyl)-2-benzofuranyl]-6-fluorobenzoate

From Intermediate 54 according to the method of Intermediate 6.

T.l.c. System A (1:3) Rf=0.4.

Intermediate 56

Methyl 2-[3-bromo-5-[(2-ethyl-5,7-dimethyl-3H-imidazo[4,5-b]pyridin-3-yl)methyl]-2-benzofuranyl]-6-fluorobenzoate From 2-ethyl-5,7-dimethyl-3H-imidazo[4,5-b]pyridine (described in European Patent Specification No. 0400974-A, published 5th Dec. 1990) and Intermediate 55 according to the method of Intermediate 32.

T.l.c. ether:ethyl acetate (1:1) Rf=0.4.

Intermediate 57

1,1-Dimethylethyl 2-fluoro-6-iodobenzoate

N,N-Dimethylformamide di-t-butyl acetal (3.8 ml, 3.2 g) was added to a stirred mixture of 2-fluoro-6-iodobenzoic acid (1.25 g) in toluene (25 ml). The mixture was then stirred at 90° for 4 h, allowed to stand at room temperature for 60 h before further dimethylformamide di-t-butyl acetal (1 ml, 0.85 g) was added and heating continued at 90° for 90 min. After cooling, the orange solution was washed with water (50 ml), brine (50 ml), 10% aqueous lithium chloride solution and 8% aqueous sodium bicarbonate solution (50 ml), dried and concentrated in vacuo to afford an orange liquid (1.9 g). Purification by chromatography eluting with System A (1:1) gave the title compound (1.37 g) as an orange liquid.

Assay Found: C,41.3; H,3.8; $C_{11}H_{12}FIO_2$ requires: C,41.0; H,3.8%.

Intermediate 58

1,1-Dimethylethyl 2-fluoro-6-(5-methyl-2-benzofuranyl)benzoate

Tetrakis(triphenylphosphine)palladium (0) (0.1 g) was added to a stirred mixture of Intermediate 51 (1.35 g) and Intermediate 57 (1.49 g) in toluene (50 ml) at 90° under a nitrogen atmosphere. After stirring at 110° for 45 min, further tetrakis(triphenylphosphine) palladium (0) (0.2 g) was added and stirring continued for 4 h at 110°. After standing overnight at room temperature, the solution was partitioned between ethyl acetate (150 ml) and water (150 ml). The separated organic phase was dried and concentrated in vacuo to afford an orange semi-solid (2.4 g). Purification by chromatography eluting with System A (1:19) afforded the title compound (0.51 g) as a viscous gum.

T.l.c. System A (1:5) Rf 0.5.

Intermediate 59

1,1-Dimethylethyl 2-[5-(bromomethyl)-2-benzofuranyl]-6-fluorobenzoate

From Intermediate 58 according to the method of Intermediate 6.

T.l.c. System A (1:4) Rf=0.45.

Intermediate 60

1,1-Dimethylethyl 2-[5-[(2-ethyl-5,7-dimethyl-3H-imidazo[4,5-b]pyridin-3-yl)methyl]-2-benzofuranyl]-6-fluorobenzoate From 2-ethyl-5,7-dimethyl-3H-imidazo[4,5-b]pyridine and Intermediate 59 according to the method of Intermediate 32.

T.l.c. ether:ethyl acetate (8:1) Rf=0.3.

Intermediate 61

Methyl 2-[5-[(2-ethyl-5,7-dimethyl-3H-imidazo[4,5-b]pyridin-3-yl)methyl]-2-benzofuranyl]-6-fluorobenzoate Intermediate 60 (0.42 g) was dissolved in trifluoroacetic acid (4 ml) at 0° and stirred at 3° for 2 h. The solution was concentrated in vacuo to afford a reddish gum which was dissolved in dichloromethane (50 ml) before being washed with water (2×50 ml), dried and concentrated in vacuo to afford a reddish gum (0.39 g). To a solution of this gum (0.39 g) in methanol (15 ml) was added a solution of diazomethane (10 mmol) in ether. Excess diazomethane was destroyed using glacial acetic acid and the mixture was concentrated in vacuo to afford, after azeotroping with toluene (40 ml), an orange gum (0.43 g). Purification by chromatography eluting with ether:ethyl acetate (1:1) afforded the title compound (0.25 g) as a pale yellow foam.

n.m.r.(CDCl$_3$) δ1.3 (t,3H), 2.62 (s,3H), 2.65 (s,3H), 2.8 (q,2H), 36.92 (s,3H), 5.55 (brs,2H), 6.87 (s,1H), 6.92 (s,1H), 7.1–7.2 (m,2H), 7.28 (m,1H), 7.4–7.6 (m,3H).

Intermediate 62

Methyl 2-[3-bromo-5-[(2-ethyl-5,7-dimethyl-3H-imidazo[4,5-b]pyridin-3-yl)methyl]-2-benzofuranyl]-6-fluorobenzoate A solution of bromine in carbon tetrachloride (1M, 0.55 ml) was added to a stirred solution of Intermediate 61 (0.25 g) in dichloromethane (20 ml) at 3°. After stirring for 3 h, further bromine in carbon tetrachloride (1M, 0.05 ml) was added and stirring continued at room temperature overnight. The orange solution was diluted with dichloromethane (30 ml), washed with aqueous sodium thiosulphate (2×30 ml) and 8% sodium bicarbonate (30 ml), dried and concentrated in vacuo to afford a yellow oil (0.31 g). Purification by chromatography eluting with ether:ethyl acetate (2:1) afforded the title compound (0.145 g) as a white solid.

n.m.r. (CDCl$_3$) δ1.32 (t,3H), 2.6–2.85 (m,8H), 3.92 (s,3H), 5.5 (brs,2H), 6.88 (s,1H), 7.1–7.2 (m,2H), 7.28 (m,1H), 7.38–7.61 (m,3H).

Intermediate 63

Methyl 2-[3-bromo-5-[(6-bromo-2-ethyl-5,7-dimethyl-3H-imidazo[4,5-b]pyridin-3-yl)methyl]-2-benzofuranyl]-6-fluorobenzoate A solution of bromine in carbon tetrachloride (0.1 ml, 1M) was added to a stirred solution of Intermediate 62 (0.14 g) in dichloromethane (15 ml) at 3°. The solution was allowed to warm to room temperature and further amounts of bromine in carbon tetrachloride (1M, 0.2 ml) and (0.15 ml, 1M) were added after 3 h and 16 h respectively. A final amount of bromine in carbon tetrachloride (1M, 0.1 ml) was added and stirring continued for 20 h. The solution was then washed with aqueous sodium thiosulphate (30 ml), water (25 ml) and 8% sodium bicarbonate (25 ml). The organic phase was then dried and concentrated in vacuo to afford the title compound (0.21 g) as a yellow gum.

T.l.c. ethyl acetate:ether (1:1) Rf=0.6.

Intermediate 64

2-Cyclopropyl-5,7-dimethyl-3H-imidazo[4,5-b]pyridine

From 2,3-diamino-4,6-dimethylpyridine (described in European Patent specification No. 0400974-A, published 5th Dec. 1990) and cyclopropanecarboxylic acid according to the method of Intermediate 12.

T.l.c. System C (100:8:1) Rf=0.28.

Intermediate 65

1,1-Dimethylethyl 2-[3-bromo-5-[(2-cyclopropyl-5,7-dimethyl-3H-imidazo[4,5-b]pyridin-3-yl)methyl]-2-benzofuranyl]benzoate From Intermediate 64 and Intermediate 24 according to the method of Intermediate 32.

T.l.c. ether:petroleum ether:acetate acid (21:9:1) Rf=0.40.

Intermediate 66

2-(5-Methyl-2-benzofuranyl)benzoic acid

Intermediate 2 (10.0 g) was suspended in glycerol and heated to 120° C. under an atmosphere of nitrogen. Solid potassium hydroxide (12.0 g) was added, in portions, and the reaction mixture was heated to 170° C. After 3 hours the mixture was cooled and poured into water (200 ml). 2M hydrochloride acid (100 ml) was added dropwise, with stirring, to the solution. The resulting yellowish solid was isolated by filtration and dried in vacuo to afford the title compound (12.05 g).
T.l.c. hexane:ethyl acetate:acetic acid (15:5:1) Rf=0.43.

Intermediate 67

(±)-3-Chloro-5-methylspiro[benzofuran-2(3H),1'(3'H)-isobenzofuran]-3'-one

Intermediate 66 (11.95 g) was dissolved in 1,4-dioxane (300 ml) and water (4 ml) was added. The mixture was placed under an atmosphere of nitrogen. N-chlorosuccinimide (7.67 g) was added to the stirred solution which was then heated at reflux for 1.5 hours. The mixture was cooled to room temperature, diluted with ethyl acetate (300 ml) and washed with brine (3×300 ml). The organic solution was concentrated in vacuo to afford a solid (20.2 g) which was triturated with methanol (350 ml) and filtered to give the title compound (7.22 g) as a white solid.
T.l.c. System F (1:3) Rf=0.49.

Intermediate 68

2-(3-Chloro-5-methyl-2-benzofuranyl)benzoic acid

Intermediate 67 (7.135 g) was suspended in toluene (250 ml) and 1,8-diazabicyclo[5.4.0]undec-7-ene (4.58 g) was added slowly over a five minute period. The suspension was warmed to 45° C. and stirred for 3 hours. The solution was then heated at reflux for 1 hour. The reaction mixture was cooled, diluted with toluene (500 ml) and shaken with hydrochloric acid (250 ml) and brine (250 ml). The organic layer was dried and concentrated in vacuo to afford the title compound (6.78 g) as a yellow solid.
T.l.c. hexane:ethyl acetate:acetic acid (15:5:1) Rf=0.50.

Intermediate 69

Methyl 2-(3-chloro-5-methyl-2-benzofuranyl)benzoate

Intermediate 68 (6.78 g) was suspended in toluene (240 ml) under an atmosphere of nitrogen. Dimethylformanide, dimethyl acetal (12.68 g) was added dropwise to the suspension over a five minute period. The temperature was raised to 80° C. and the resulting solution was stirred overnight. The reaction mixture was cooled, diluted with toluene (250 ml) and washed with portions of aqueous lithium chloride (10% w/v; 2×150 ml). The organic solution was then dried and concentrated in vacuo to afford a yellow oil (7.08 g). Purification by flash chromatography eluting with System F (1:12) gave the title compound (5.69 g) as a pale yellow oil.
T.l.c. System F (1:3) Rf=0.54.

Intermediate 70

Methyl 2-[5-(bromomethyl)-3-chloro-2-benzofuranyl]benzoate

From Intermediate 69 according to the method of Intermediate 6.
T.l.c. System F (1:3) Rf=0.48.

Intermediate 71

Methyl 2-[3-chloro-5-[(2-ethyl-5,7-dimethyl-3H-imidazo[4,5-b]pyridin-3-yl)methyl]-2-benzofuranyl]benzoate From 2-ethyl-5,7-dimethyl-3H-imidazo[4,5-b]pyridine and Intermediate 70 according to the method of Intermediate 32.
T.l.c. ether Rf=0.31.

Intermediate 72

2,2,2-Trifluoro-1-[5-methyl-2-[(2-nitrophenyl)methoxy]phenyl]ethanone

A solution of 2-nitro benzyl alcohol (6.9 g) in 1,4-dioxane (100 ml) was added to a mixture of 2,2,2-trifluoro-1-[2-hydroxy-5-methyl)phenyl]ethanone (described in European Patent Specification No. 0434249-A, published 26th Jun. 1991) (6.23 g), sodium iodide (0.458 g) and potassium carbonate (4.64 g) in N,N-dimethylacetamide (60 ml). After stirring for 18 h, distilled water (500 ml) was added and the resultant slurry stirred for 2 h. The solid was collected by filtration, washed with 1,4-dioxane/water (1:1) (300 ml), water (3×50 ml) and oven dried to give the title compound as a pale yellow solid (7.37 g).
T.l.c. System A (1:6) Rf 0.38.

Intermediate 73

2,3-Dihydro-5-methyl-2-(2-nitrophenyl)-3-(trifluoromethyl)-3-benzofuranol (cis & trans diastereoisomers)

Sodium methoxide (246 mg) was added to a cooled (0° C.) solution of the Intermediate 72 (4.363 g) in N,N-dimethylacetamide (40 ml) and stirred for 3 h. Distilled water (100 ml) was added and the aqueous layer extracted with ethyl acetate (2×100 ml; 80 ml). The combined organic extracts were washed with water (80 ml) and 10% aqueous lithium chloride solution (2×100 ml), dried and the solvent removed in vacuo to give an oil. Purification by flash column chromatography eluting with System A (1:10→1:3) gave the title compounds as pale yellow solids (1.33 g; 2.11 g).
T.l.c. System A (1:3) Rf 0.42 and Rf 0.21,

Intermediate 74

5-(Bromomethyl)-2-(2-nitrophenyl)-3-(trilfluoromethyl)benzofuran

A solution of the diastereoisomers of Intermediate 73 (5.727 g) in acetic anhydride (50 ml) and conc. sulphuric acid (5 drops) was heated at reflux for 4.5 h. After cooling the solution was concentrated in vacuo, diluted with ethyl acetate (100 ml), washed with 8% sodium bicarbonate (2×100 ml) and dried. The solvent was removed in vacuo to give the title compound as a brown solid (5.69 g).
T.l.c. System A (1:1) Rf 0.61.

Intermediate 75

5-(Bromomethyl)-2-(2-nitrophenyl)-3-(trifluoromethyl)benzofuran

From Intermediate 74 according to the method of Intermediate 6.

T.l.c. System A (1:3) Rf=0.33.

Intermediate 76

2-Ethyl-5,7-dimethyl-3-[[2-(2-nitrophenyl)-3-(trifluoromethyl)-5-benzofuranyl]methyl]-3H-imidazo[4,5-b]pyridine From 2-ethyl-5,7-dimethyl-3H-imidazo[4,5-b]pyridine and Intermediate 75 according to the method of Intermediate 32.

T.l.c. ether Rf=0.34.

Intermediate 77

2-[5-[(2-Ethyl-5,7-dimethyl-3H-imidazo[4,5-b]pyridin-3-yl)methyl]-3-(trifluoromethyl)-2-benzofuranyl]benzenamine Iron powder (157 mg) was added to a solution of Intermediate 76 (369 mg) in ethanol (20 ml), acetic acid (6 ml) and water (6 ml) and the mixture heated at reflux for 3 hours. The red mixture was cooled, filtered and the residue washed with ethanol (2×50 ml). The combined filtrate and washings were concentrated in vacuo, diluted with water (100 ml) and the pH adjusted to 9-10 by adding 2M sodium carbonate solution. The aqueous layer was extracted with ethyl acetate (3×150 ml) and the combined organic extracts were dried and concentrated in vacuo to give the title compound as a yellow solid (200 mg).

T.l.c. ether Rf=0.28.

Intermediate 78

1,1-Dimethylethyl [2-[3-bromo-5-[(2-ethyl-7-methyl-3H-imidazo[4,5-b]pyridin-3-yl)methyl]-2-benzofuranyl]phenyl]carbamate From 2-ethyl-7-methyl-3H-imidazo[4,5-b]pyridine (described in European Patent Specification No. 0400974-A, published 5th Dec. 1990) and 1,1-dimethylethyl [2-[3-bromo-5-(bromomethyl)-2-benzofuranyl]phenyl]carbamate (described in European Patent Specification No. 0434249-A, published 26th Jun. 1991) according to the method of Intermediate 15.

T.l.c. System G (16:1) Rf=0.71.

Intermediate 79

3-[[2-(2-Aminophenyl)-3-bromo-5-benzofuranyl]methyl]-2-ethyl-7-methyl-3H-imidazo[4,5-b]pyridine From Intermediate 78 according to the method of Intermediate 40.

T.l.c. System G (16:1) Rf=0.51.

EXAMPLE 1

3-[[3-Bromo-2-[2-(1H-tetrazol-5-yl)phenyl]-5-benzofuranyl]methyl]-2-butyl-1H-benzimidazole Conc. HCl (0.4 ml) was added to a suspension of Intermediate 7 (1 g) in methanol (25 ml). The solid gradually dissolved and after 15 min the solution was concentrated xn vacuo at 0°. The resultant crystals (220 mg) were filtered off and the filtrate added to water (75 ml). The white precipitate was filtered off washed with water, THF and ether and dried to give the title compound.

Assay Found: C,59.7; H, 4.7; N, 14.5, $C_{27}H_{23}BrN_6O \cdot H_2O \cdot 0.5\ C_4H_8O$ requires C, 59.9; H, 5.0; N, 14.45.

T.l.c. System C (200:8:1) Rf 0.60.

EXAMPLE 2

7-[[-3-Bromo-2-[2-(1H-tetrazol-5-yl)phenyl]-5-benzofuranyl]methyl]-8-butyl-7H-purine Intermediate 10 (400 mg), was added to methanol (10 ml) and concentrated HCl (0.1 ml), and the mixture stirred for 20 min. 2N sodium hydroxide was added to ca pH12, and the solvent was evaporated in vacuo. The residue was partitioned between water (100 ml) and ether (100 ml). The aqueous layer was further washed with ether (50 ml) and then acidified with 2N HCl to ca pH3. This was then extracted with ethyl acetate (3×150 ml), and the combined extracts were washed with water (50 ml) and brine (50 ml), dried and evaporated in vacuo to give a white solid. This was triturated with ether to give the title compound as a white solid (181 mg).

T.l.c. System G (10:1) Rf 0.74.

mp 211°-213° C.

EXAMPLE 3

3-[[3-Bromo-2-[2-(1H-tetrazol-5-yl)phenyl]-5-benzofuranyl]methyl]-5-chloro-2-ethyl-3H-imidazo[4,5-b]pyridine A solution of Intermediate 15 (260 mg), ethanol (10 ml) and concentrated hydrochloric acid (0.2 ml) was stirred at room temperature for 18 hours. The pH was adjusted to pH9 (2N NaCO₃) and the solvent removed n vacuo. The residue was partitioned between water (50 ml) and ether (3×20 ml), the aqueous layer was acidified to pH 5.5 (2NHCl) and then extracted with ethyl acetate (3×20 ml). The remaining solid was removed by filtration and dried to afford the title compound as a white solid (50 mg).

m.p. 162°-165° C.

T.l.c. System A (80:20:2) Rf=0.56.

Similarly prepared were:

EXAMPLE 4

3-[[3-Bromo-2-[2-(1H-tetrazol-5-yl)phenyl]-5-benzofuranyl]methyl]-5-chloro-2-cyclopropyl-3H-imidazo[4,5-b]pyridine m.p. 175°-180° C.

T.l.c. System C (80:20:1) Rf=0.16.

From Intermediate 16.

EXAMPLE 5

5-Bromo-3-[[3-bromo-2-[2-(1H-tetrazol-5-yl)phenyl]-5-benzofuranyl]methyl]-2-ethyl-3H-imidazo[4,5-b]pyridine m.p. 163°-165° C.

T.l.c. System C (80:20:1) Rf=0.54.

From Intermediate 17.

EXAMPLE 6

5-Bromo-1-[[3-bromo-2-[2-(1H-tetrazol-5-yl)phenyl]-5-benzofuranyl]methyl]-2-ethyl-1H-imidazo[4,5-b]pyridine MH+(calc) 577.9.

MH+(obs) 578.0.

n.m.r. (250 MHz, DMSOd₆) δ1.31(t,3H), 2.98 (q,2H), 5.72 (s,2H), 7.14 (dd,1H), 7.35(s,1H), 7.48(dd,2H), 7.8–8.1(m,5H).

From Intermediate 18.

EXAMPLE 7

3-[[3-Bromo-2-[2-(1H-tetrazol-5-yl)phenyl]-5-benzofuranyl]methyl]-2-ethyl-N-methyl-3H-imidazo[4,5-b]pyridine-5-carboxamide MH+(calc) 557.0
MH+(obs) 557.0
n.m.r. (250 MHz, CD₃OD) δ1.31 (t,3H), 2.92 (q,2H), 3.0 (d,3H), 5.78 (s,2H), 7.20(dd,1H), 7.32 (d,1H), 7.41 (d,1H), 7.60 (m,2H), 7.81 (m,2H), 8.90 (q, 1H).

From Intermediate 21.

EXAMPLE 8

3-[[3-Bromo-2-[2-(1H-tetrazol-5-yl)phenyl]-5-benzofuranyl]methyl]-5,7-dimethyl-2-ethyl-3H-imidazo[4,5-b]pyridine m.p. 215°–220° C. (dec).
T.l.c. methanol:ethyl acetate (1:9) Rf=0.50.
From Intermediate 22.

EXAMPLE 9

3-[[3-Bromo-2-[2-(1H-tetrazol-5-yl)phenyl]-5-benzofuranyl]methyl]-2-ethyl-3H-imidazo[4,5-b]pyridine-5-carboxylic acid A mixture of Intermediate 20 (100 mg), conc hydrochloric acid (1.25 ml) and acetic acid (1.25 ml) was heated at reflux for 3 h. The mixture was cooled and adjusted to pH12 with 2N aqueous sodium hydroxide, extracted with ether (3×20 ml) and the extracts discarded. The aqueous phase was acidified to pH5 with 2N hydrochloric acid and extracted with ethyl acetate (4×30 ml). The combined extracts were dried and concentrated in vacuo to give the title compound as a yellow solid (45 mg).

m.p. 185°–190° C.
T.l.c. dichloromethane:ethanol (3:2) Rf=0.30.

EXAMPLE 10

2-[3-Bromo-5-[(5,7-dimethyl-2-ethyl-3H-imidazo[4,5-b]pyridin-3-yl)methyl]-2-benzofuranyl]benzoic acid Trifluoroacetic acid (2 ml) was added to a stirred solution of Intermediate 25 (750 mg) in dichloromethane (20 ml) at 0° C. The solution was allowed to warm to room temperature and was stirred for 18 hours. The solution was concentrated in vacuo, dichloromethane (50 ml) was added and the mixture washed with water (3×40 ml). The organic solution was dried and concentrated in vacuo. The residue was purified by flash column chromatography, eluting with ether:petroleum ether (4:1) containing 1% acetic acid, to give the title compound as a white solid (460 mg).

m.p. 145°–148° C.
T.l.c ether:petroleum ether:acetic acid (80:20:1) Rf=0.15.

EXAMPLE 11

N-[2-[3-Bromo-5-[(5,7-dimethyl-2-ethyl-3H-imidazo[4,5-b]pyridin-3-yl)methyl]-2-benzofuranyl]-phenyl]trifluoromethanesulphonamide Trifluoroacetic acid (1.25 ml) was added to a solution of Intermediate 26 (1.00 g) in dichloromethane (25 ml) and stirred at 0°–5° C., under nitrogen, for 24 h. 2N aqueous sodium bicarbonate (40 ml) was added and the organic phase separated, dried and filtered. Triethylamine (0.25 ml) was added and the solution cooled to −70° C. under nitrogen. A solution of trifluoromethanesulphonic anhydride (1M in dichloromethane; 1.75 ml) was added dropwise and the solution then allowed to warm to room temperature. The solution was concentrated in vacuo, water (50 ml) and aqueous sodium hydroxide (2N; 10 ml) were added and the mixture washed with ether (2×50 ml). The aqueous phase was acidified to pH 5.5 (2N HCl) and extracted with ethyl acetate (20 ml). The extract was dried and concentrated in vacuo. Trituration with System A (1:2) gave the title compound (210 mg) as a white powder, m.p. 90°–95° C.

T.l.c. ether Rf=0.2.

Examples 12 to 14 and 26 and 27 in Table 3 were prepared according to the method of Example 3 (Equation 3):

Equation 3

Examples 15 to 21 in Table 4 were prepared according to the method of Example 10 (Equation 4):

Equation 4

-continued

Equation 4

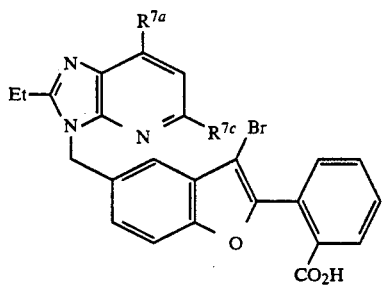

EXAMPLE 22

3-[[3-Bromo-2-[2-(1H-tetrazol-5-yl)phenyl]-5-benzofuranyl]methyl]-2-ethyl-7-methyl-3H-imidazo[4,5-b]pyridine-5-carboxylic acid Intermediate 34 (1.0 g) was stirred in methanol (30 ml) and sodium hydroxide (2M; 15 ml) for 4 days at room temperature. The mixture was diluted with distilled water and extracted with ethyl acetate (which removed the substantial amounts of unreacted starting material). The aqueous layers were acidified to pH1 with dilute hydrochloric acid and extracted with ethyl acetate. This was washed with brine and dried. Column chromatography eluting with dichloromethane:methanol:acetic acid (100:15:1) gave after evaporation the title compound as a white solid (170 mg).

T.l.c. System G (9:1) Rf 0.13 (streak).

n.m.r.(CD$_3$OD) δ1.29 (t,3H), 2.70 (s,3H), 2.94 (q,2H), 5.77 (s,2H), 7.10–7.37 (m,3H), 7.66–7.70 (m,2H), 7.82–7.90 (m,2H), 7.99 (s,1H).

EXAMPLE 23

Ethyl 3-[[3-bromo-2-[2-[[(trifluoromethyl)sulphonyl]amino]-phenyl]-5-benzofuranyl]methyl]-2-ethyl-7-methyl-3H-imidazo[4,5-b]pyridine-5-carboxylate Trifluoromethanesulphonic anhydride (1M in dichloromethane; 1.65 ml) was added dropwise to a solution of Intermediate 41 (880 mg) and triethylamine (0.3 ml) in dry dichloromethane (15 ml) at −78° under nitrogen. The mixture was stirred at −70° to −60° for 1 h, then water (4 ml) added-dropwise and the mixture allowed to warm to room temperature. The mixture was partitioned between water (30 ml) and dichloromethane (3×25 ml) and the combined organic extracts washed with brine (1×30 ml) and dried. The solvent was evaporated to give a pale yellow foam (1.08 g) which was purified by short-path column chromatography on silica (Merck 7729;30 g) eluting with System G (200:1) to give the title compound as a colourless foam (524 mg).

T.l.c. ether Rf=0.5.

n.m.r. (CDCl$_3$) δ1.35 (t,3H), 1.46 (t,3H), 2.73 (s,3H), 2.89 (q,2H), 4.48 (q,2H), 5.70 (s,2H), 7.26 (dd,1H), 7.45 (m,3H), 7.54 (ddd,1H), 7.69 (dd,1H), 7.82 (dd,1H), 7.98 (s,1H).

EXAMPLE 24

3-[[3-Bromo-2-[2-[[(trifluoromethyl)sulphonyl]amino]phenyl]-5-benzofuranyl]methyl]-2-ethyl-7-methyl-3H-imidazo[4,5-b]pyridine-5-carboxylic acid, hydrochloride From the product of Example 23 according to the method of Intermediate 38.

m.p. 118°–124° C.,

T.l.c. dichloromethane:methanol:acetic acid (50:1:1) Rf=0.3.

EXAMPLE 25

3-[[3-Bromo-2-[2-[[(trifluoromethyl)sulphonyl]amino]-phenyl]-5-benzofuranyl]methyl]-2-ethyl-7-methyl-3H-imidazo[4,5-b]pyridine-5-methanol From the product of Example 23 according to the method of Intermediate 47.

m.p. 125°–130° C.,

T.l.c. ethyl acetate Rf=0.38.

EXAMPLE 28

2-[3-Bromo-5-[(2-ethyl-5,7-dimethyl-3H-imidazo[4,5-b]pyridin-3-yl)methyl]-2-benzofuranyl]-6-fluorobenzoic acid A mixture of Intermediate 56 (0.21 g) in methanol (25 ml) containing 2N sodium hydroxide (5 ml) was stirred at reflux for 2 h. After cooling, the mixture was acidified with 2N hydrochloric acid to pH1 before being extracted with ethyl acetate (4×25 ml). The combined organic extracts were dried and concentrated in vacuo to afford the title compound as an off-white solid (0.146 g), m.p. 191°–194°.

n.m.r.(DMSOd$_6$) δ1.32 (t,3H), 2.65 (s,6H), 3.2 (q,2H), 5.82 (brs,2H), δ7.3–7.8 (m,7H).

EXAMPLE 29

2-[3-Bromo-5-[(6-bromo-2-ethyl-5,7-dimethyl-3H-imidazo[4,5-b]pyridin-3-yl)methyl]-2-benzofuranyl]-6-fluorobenzoic acid A mixture of Intermediate 63 (0.21 g) in methanol (20 ml) and 2N sodium hydroxide (5 ml) was stirred at reflux for 2 h. After cooling, the mixture was acidified employing 2N hydrochloric acid to pH1, brine (15 ml) added before the whole was extracted with ethyl acetate (2×20 ml). The combined organic extracts were dried and concentrated in vacuo to afford a solid (0.11 g). This solid was redissolved in methanol (15 ml), 2N sodium hydroxide (7 ml) added and the mixture stirred at reflux for 2 h. After cooling, the solution was acidified with 2N hydrochloric acid, brine (15 ml) added and then extracted with ethyl acetate (4×20 ml). The combined organic extracts were dried and concentrated in vacuo to afford the title compound (0.075 g) as a pale yellow solid, m.p. 223°–225° C.

n.m.r.(DMSOd$_6$) δ1.28 (t,3H), 2.66 (s,3H), 2.73 (s,3H), 2.92 (q,2H), 5.68 (brs,2H), 7.25 (dd,1H), 7.5–7.8 (m,5H).

EXAMPLE 30

2-[3-Bromo-5-[(2-cyclopropyl-5,7-dimethyl-3H-imidazo[4,5-b]pyridin-3-yl)methyl]-2-benzofuranyl]benzoic acid From Intermediate 65 according to the method of Example 10.

m.p. 137°–140° C.

T.l.c. ether:petroleum ether:acetic aicd (21:9:1) Rf=0.17.

EXAMPLE 31

2-[3-Chloro-5-[(2-ethyl-5,7-dimethyl-3H-imidazo[4,5-b]pyridin-3-yl)methyl]-2-benzofuranyl]benzoic acid From Intermediate 71 according to the method of Example 28.
m.p. 230°-232° C.
T.l.c. ether:ethyl acetate (60:1) Rf=0.38.

EXAMPLE 32

N-[2-[5-[(2-Ethyl-5,7-dimethyl-3H-imidazo[4,5-b]pyridin-3-yl)methyl]-3-(trifluoromethyl)-2-benzofuranyl]-phenyl]trifluoromethanesulphonamide From Intermediate 77 according to the method of Example 23.
T.l.c. ether Rf=0.25.
Mass Spec. MH+ (calc.) 597.0; MH+ (obs.) 597.0.

EXAMPLE 33

N-[2-[3-Bromo-5-[(2-ethyl-7-methyl-3H-imidazo[4,5-b]pyridin-3-yl)methyl]-2-benzofuranyl]phenyl]trifluoromethanesulphonamide From Intermediate 79 according to the method of Example 23.
m.p. 97°-100° C.
T.l.c. ether:acetic acid (99:1) Rf=0.33.

EXAMPLE 34

Methyl 3-[[3-bromo-2-[2-[[(trifluoromethyl)sulphonyl]amino]-phenyl]-5-benzofuranyl]methyl]-2-ethyl-3H-imidazo[4,5-b]pyridine-5-carboxylate From Intermediate 40 according to the method of Example 23.
T.l.c. System G (9:1) Rf=0.56.
n.m.r. (CDCl$_3$) δ1.38 (t,3H), 2.85 (q,2H), 4.11 (s,3H), 5.70 (s,2H), 7.25 (dd,1H), 7.4-7.5 (m,3H), 7.55 (ddd,1H), 7.68 (dd,1H), 7.82 (dd,1H), 8.05 & 8.15 (AB,2H).

EXAMPLE 35

3-[[3-Bromo-2-[2-[[(trifluoromethyl)sulphonyl]amino]-phenyl]-5-benzofuranyl]methyl]-2-ethyl-3H-imidazo[4,5-b]pyridine-5-methanol From the product of Example 34 according to the method of Intermediate 44.
m.p. 165°-170° C.
T.l.c ethyl acetate Rf=0.28.

The compounds of the invention are tested in vitro for angiotensin II receptor antagonism. Aortic strips are obtained from male New Zealand white rabbits and prepared for recording isometric contractions in response to cumulative addition of angiotensin II. The potencies of test antagonists are assessed by measuring their abilities to displace the angiotensin II cumulative concentration response curve. The method used is that of Ackerly et al., *Proc. Natl. Acad. Sci.*, 74(12), pp5725-28 (1977) with the exception that the final composition of the physiological salt solution is as given below in Table 1:

TABLE 1

| Ingredient | Amount (mM) |
|---|---|
| Na$^+$ | 143.4 |
| K$^+$ | 5.9 |
| Mg$^{2+}$ | 0.6 |
| Ca$^{2+}$ | 1.3 |
| Cl$^-$ | 124.5 |
| HPO$_4^-$ | 1.2 |
| SO$_4^{2-}$ | 0.6 |
| HCO$_3^-$ | 25.0 |
| glucose | 11.1 |
| indomethacin | 0.005 |
| ascorbic acid | 0.1 |

The tissues are initially challenged with K+ (80 mM) and then washed at 0, 5, 10 and 15 minutes after the response to K+ has plateaued. After a further 45 minutes an angiotensin II cumulative response curve is constructed (0.1 nM to 0.1 μM in 10-fold increments) and the tissues are washed as before. A second, third and fourth angiotensin II cumulative response curve (0.1 nM to 0.1 μM in 3-fold increments) is then constructed at hourly intervals (15 minutes washing after each curve followed by 45 minutes equilibration). The compounds of the invention (30 μM) are tested for angiotensin II receptor antagonism by application 45 minutes before construction of the fourth angiotensin II curve. The third and fourth angiotensin II curves are expressed graphically and a concentration ratio (CR) is calculated by dividing the angiotensin II EC$_{50}$ value obtained in the presence of the test antagonist (i.e. fourth curve) by the angiotensin II EC$_{50}$ value obtained in the absence of the test antagonist (i.e. third curve).

The potency of the test antagonist is expressed as a pKb which is calculated from the equation:

$$pKb = -\log\left[\frac{CR-1}{[\text{antagonist}]}\right]$$

which is a rearrangement of equation 4 described by Furchgott, in *Handbook of Exp. Pharmacol.*, 33, p290 (1972) (eds. Blaschko and Muscholl).

If a compound supresses the maximum response to angiotensin II, a pKb is estimated using the double reciprocal plot technique for insurmountable antagonists, described by T. P. Kenakin, *Pharmacol. Rev.*, 36(3), pp165-222 (esp. 203-204) (1984).

Compounds of the invention will desirably exhibit a pKb in the range between 5 and 12. Thus we have found that the compounds of the invention inhibit the action of the hormone angiotensin II and are therefore useful in the treatment of conditions in which it is desirable to inhibit angiotensin II activity. In particular, the compounds of the Examples are active in the above test.

There is thus provided as a further aspect of the invention a compound of general formula (I) or a physiologically acceptable salt, solvate or metabolically labile ester thereof for use in the treatment of conditions associated with excessive or unregulated angiotensin II activity.

In a further or alternative aspect of the invention there is provided a compound of general formula (I) or a physiologically acceptable salt, solvate or metabolically labile ester thereof for the manufacture of a therapeutic agent for the treatment of conditions associated with excessive or unregulated angiotensin II activity.

There is also provided in a further or alternative aspect of the invention a method for the treatment of conditions associated with excessive or unregulated angiotensin II activity in a mammal including man comprising administration of an effective amount to a mammal in need of such treatment a compound of general formula (I) or a physiologically acceptable salt, solvate or metabolically labile ester thereof.

In addition, by virtue of their antagonistic activity at angiotensin II receptors, compounds of the present invention will be of value in the treatment of conditions associated with activation of the Renin-Angiotensin System.

There is thus provided a further aspect of the present invention a compound of general formula (I) or a physiologically acceptable salt, solvate or metabolically labile ester thereof for use in the treatment of a condition associated with activation of the Renin-Angiotensin system.

In a further or alternative aspect of the present invention there is provided a compound of general formula (I) or a physiologically acceptable salt, solvate or metabolically labile ester thereof for the manufacture of a therapeutic agent for the treatment of a condition associated with activation of the Renin-Angiotensin System.

There is also provided in a further or alternative aspect of the present inventions a method for the treatment of a condition associated with the activation of the Renin-Angiotensin System in a mammal including man comprising administration of an effective amount to a mammal in need of such treatment of a compound of general formula (I) or a physiologically acceptable salt, solvate or metabolically labile ester thereof.

The following examples illustrate pharmaceutical formulations according to the invention. The term "active ingredient" is used herein to represent a compound of formula (I).

Pharmaceutical Example 1

| Oral Tablet A | |
| --- | --- |
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

Pharmaceutical Example 2

| Oral Tablet B | |
| --- | --- |
| Active Ingredient | 500 mg |
| Lactose | 100 mg |
| Maize starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

Pharmaceutical Example 3

| Inhalation Cartridge | |
| --- | --- |
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

Pharmaceutical Example 4

| Injection Formulation | % w/v |
| --- | --- |
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

TABLE 1

| | | (see Equation 1) | | | |
| --- | --- | --- | --- | --- | --- |
| Int. No. | From: | $R^{3a}$ | $R^{7a}$ | $R^{7c}$ | Data |
| 33 | Ints. 30 + *1 | —NHt—BOC | H | $CO_2Me$ | T.l.c. ether Rf = 0.14 |
| 34 | Ints. 31 + 6 | Tet—P | Me | $CO_2Et$ | T.l.c. ether Rf = 0.28 |
| 35 | Ints. 31 + *1 | —NHt—BOC | Me | $CO_2Et$ | T.l.c. ether Rf = 0.40 |
| 36 | Ints. 31 + 24 | —$CO_2$t—Bu | Me | $CO_2Et$ | T.l.c. ether Rf = 0.50 |
| 37 | Ints. 30 + 6 | Tet—P | H | $CO_2Me$ | T.l.c. System F (2:1) Rf = 0.30 |

TABLE 1-continued

| | | (see Equation 1) | | | |
|---|---|---|---|---|---|
| Int. No. | From: | $R^{3a}$ | $R^{7a}$ | $R^{7c}$ | Data |
| 80 | Ints. 31 + 70 | —$CO_2Me$ | Me | $CO_2Et$ | T.l.c. System F (3:2) Rf = 0.34 |
| 83 | Ints. 31 + 82 | —$CO_2t$—Bu | Me | $CO_2Et$ | T.l.c. ether Rf = 0.30 |

TABLE 2

| | | (see Equation 2) | | | |
|---|---|---|---|---|---|
| Int. No. | From: | $R^{3a}$ | $R^{7a}$ | $R^{7c}$ | Data |
| 45 | Int. 37 | Tet—P | H | $CO_2Me$ | T.l.c. System G (14:1) Rf = 0.31 |
| 46 | Int. 32 | —$CO_2t$—Bu | H | $CO_2Me$ | Assay *2 |
| 47 | Int. 36 | —$CO_2t$—Bu | Me | $CO_2Et$ | T.l.c. ether Rf = 0.12 |
| 84 | Int. 83 | —$CO_2t$—Bu | Me | $CO_2Et$ | T.l.c. ether:ethyl acetate (1:1) Rf = 0.25 |

TABLE 3

| | | | | (see Equation 3) | | |
|---|---|---|---|---|---|---|
| | | | | Data | | |
| | | | | T.l.c. | | |
| Ex. No. | From: | $R^{7a}$ | $R^{7c}$ | System | Rf = | Other |
| 12 | Int. 27 | H | $CONH_2$ | C (80:15:1) | 0.19 | m.p. 250–255° C. |
| 13 | Int. 34 | Me | $CO_2H$ | E (9:1) | 0.31 | n.m.r. *3 |
| 14 | Int. 45 | H | $CH_2OH$ | G (9:1) | 0.4 | Mass spec: |
| | | | | | | $MH^+$ (calc) 530 |
| | | | | | | $MH^+$ (obs) 530 |
| 26 | Int. 43 | Me | H | G (16:1) + 1% acetic acid | 0.55 | m.p. 165–170° C. |
| 27 | Int. 50 | Me | $C(CH_3)_2OH$ | I (1:9) | 0.25 | m.p. 135–138° C. (decomp). |

TABLE 4

| | | | | (see Equation 4) | | |
|---|---|---|---|---|---|---|
| | | | | Data | | |
| | | | | T.l.c. | | |
| Ex. No. | From: | $R^{7a}$ | $R^{7c}$ | System | Rf = | Other |
| 15 | Int. 38 | H | $CO_2H$ | | | m.p. 240–245° C. (decomp) |
| | | | | | | n.m.r. *4 |
| 16 | Int. 39 | Me | $CO_2H$ | | | Assay *5 |
| | | | | | | n.m.r. *6 |
| 17 | Int. 42 | Me | H | G (10:1) | 0.5 | m.p. 243–245° C. |
| 18 | Int. 46 | H | $CH_2OH$ | H (9:1) | 0.47 | m.p. 252–253° C. |
| 19 | Int. 47 | Me | $CH_2OH$ | E (10:1) | 0.12 | m.p. 138–143° C. |
| 20 | Int. 48 | H | $CONH_2$ | | | m.p. 234–237° C. |
| | | | | | | n.m.r. *7 |
| 21 | Int. 49 | Me | $CONH_2$ | | | m.p. 130–134° C. |
| | | | | | | n.m.r. *8 |

*1 1,1-dimethylethyl [2-[3-bromo-5-(bromomethyl)-2-benzofuranyl]phenyl]carbamate (described in European Patent specification No. 0434249A, published 26th June 1991).
*2 Assay Found: C, 61.6; H, 5.0; N, 7.5;
$C_{29}H_{27}BrN_3O_4$ requires: C, 62.0; H, 4.85; N, 7.5%
*3 n.m.r. ($CD_3OD$) δ1.28(3H, t), 2.66(3H, s), 2.90(2H, q), 4.76(2H, s), 5.66(2H, s), 7.16(1H, dd), 7.28–7.32(3H, m), 7.57(2H, m), 7.8(2H, m).
*4 n.m.r. ($CDCl_3$) δ1.31(3H, t), 2.95(2H, q), 5.76(2H, s), 7.27(1H, dd), 7.50–7.75(5H, m), 7.97(1H, d), 8.05–8.17(AB, 2H).
*5 Assay Found: C, 46.1; H, 2.9; N, 5.4;
$C_{26}H_{20}BrN_3O_5.2.3CF_3CO_2H$ requires: C, 46.1; H, 2.8; N, 5.3%
*6 n.m.r. ($CD_3OD$) δ1.36(3H, t), 2.77(3H, s), 3.16(2H, q), 5.91(2H, s), 7.37(1H, dd), 7.50(1H, d), 7.59–7.72(4H, m), 8.0(1H, dd), 8.15(1H, s).
*7 n.m.r. ($CD_3OD$) δ1.42(3H, t), 3.26(2H, q), 5.97(2H, s), 7.42(1H, dd), 7.52(1H, d), 7.55–7.75(4H, m), 8.00(1H, dd).
*8 n.m.r. ($DMSOd_6$) δ1.31(3H, t), 2.66(3H, s), 3.00(2H, q), 4.90(1H, br. s), 5.82(2H, s), 7.34(1H, dd), 7.60–7.77(6H, m), 7.90–7.98(2H, m), 8.30(1H, s).

Intermediate 81

1,1-Dimethylethyl 2-(3-chloro-5-methyl-2-benzofuranyl)benzoate

From Intermediate 68 according to the method of Intermediate 57.

n.m.r. ($CDCl_3$) δ1.3 (s,9H), 2.5 (s,3H), 7.17 (dd,1H), 7.34 (d,1H), 7.4 (br.s,1H), 7.48–7.62 (m,2H), 7.72 (dd,1H), 7.9 (dd,1H).

Intermediate 82

1,1-Dimethylethyl 2-(5-bromomethyl-3-chloro-2-benzofuranyl)benzoate

From Intermediate 81 according to the method of Intermediate 6.

T.l.c. ether Rf=0.85.

EXAMPLE 36

3-[[2-(2-carboxyphenyl)-3-chloro-5-benzofuranyl]methyl]-2-ethyl-7-methyl-3H-imidazo[4,5-b]pyridine-5-carboxylic acid A mixture of Intermediate 80 (495 mg), methanol (8 ml) and 2N sodium hydroxide (8 ml) was stirred at room temperature for 4 hours. The reaction was evaporated and diluted with water (10 ml) before being acidified (pH3) with 2N hydrochloric acid. The resulting fine precipitate was extracted with ethyl acetate (2×40 ml), dried and evaporated to give the title compound as a white solid (328 mg).

T.l.c. System E (100:1) Rf=0.6.

n.m.r. (DMSOd$_6$) δ1.3 (t,3H), 2.66 (s,3H), 2.93 (q,2H), 5.74 (s,2H), 7.26 (m,1H), 7.58–7.79 (m,5H), 7.9–7.96 (m,2H).

EXAMPLE 37

N-[2-[3-Bromo-5-[[2-ethyl-5-[2-(hydroxypropyl)]-7-methyl-3H-imidazo[4,5-b]pyridin-3-yl]methyl]-2-benzofuranyl]phenyl]trifluoromethanesulphonamide From the product of Example 23 according to the method of Intermediate 50.

m.p. 158°–164° C.

T.l.c. ethyl acetate Rf=0.61.

EXAMPLE 38

2-[3-Chloro-5-[(2-ethyl-5-hydroxymethyl-7-methyl-3H-imidazo[4,5-b]pyridin-3-yl)methyl]2-benzofuranyl]benzoic acid Trifluoroacetic acid (3 ml) was added to a cooled stirred solution of Intermediate 84 (0.83 g) in dichloromethane (55 ml) at 3° C. The reaction mixture was allowed to warm to room temperature and stirred for 2 hours. The mixture was concentrated, in vacuo, to afford a residue which was dissolved in dichloromethane (50 ml) before being washed with water (1×50 ml), dried and concentrated in vacuo to afford a pale yellow viscous oil (1.2 g). This material was dissolved in trifluoroacetic acid (4 ml) and the solution was stirred at room temperature for 3.5 hours before being diluted with ethanol (10 ml). Aqueous 2N sodium hydroxide (28.3 ml) was added dropwise to the ice cooled solution and the mixture was stirred for 10 minutes at room temperature. The reaction mixture was cooled in ice, acidified to pH3 with 2N hydrochloric acid and then diluted with brine (50 ml) and shaken with dichloromethane (2×60 ml). The dichloromethane extracts were combined, washed with water (2×50 ml) and the organic layer dried. Concentration in vacuo gave the title compound (0.63 g) as an off-white powder.

n.m.r. (DMSOd$_6$) δ1.28 (t,3H), 2.6 (s,3H), 2.88 (q,2H), 4.65 (s,2H), 5.64 (s,2H), 7.22 (d,2H), 7.49 (s,1H), 7.58–7.75 (m,4H), 7.93 (d,1H).

Mass spec—MH+ (calc)=476.0; MH+ (obs)=476.0.

We claim:

1. A compound of formula (I):

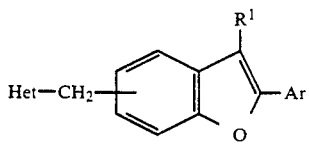

(I)

or a physiologically acceptable salt, solvate or metabolically labile ester thereof wherein $R^1$ represents a hydrogen atom, a halogen atom, $C_{1-6}$alkyl, $C_{2-6}$alkenyl, fluoro$C_{1-6}$alkyl, $C_{1-6}$alkoxy, —CHO, —CO$_2$H or —COR$^2$;

Ar represents the group

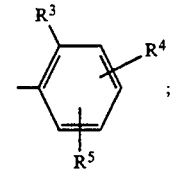

$R^2$ represents $C_{1-6}$alkyl, $C_{2-6}$alkenyl, $C_{1-6}$alkoxy or a group —NR$^{15}$R$^{16}$;

$R^3$ represents —CO$_2$H, —NHSO$_2$CF$_3$ or a C-linked tetrazolyl group;

$R^4$ and $R^5$ which may be the same or different each independently represent a hydrogen atom, a halogen atom or $C_{1-6}$alkyl;

Het represents the group

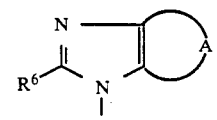

A, when read in a clockwise or anti-clockwise direction, represents

$R^6$ represents a hydrogen atom, $C_{1-6}$alkyl, $C_{2-6}$alkenyl, $C_{1-6}$alkylthio, $C_{1-6}$alkoxy, $C_{3-7}$cycloalkyl, or $C_{3-7}$cycloalkylC$_{1-4}$alkyl;

$R^{7a}$, $R^{7b}$ and $R^{7c}$, which may be the same or different, each independently represents a hydrogen atom, a halogen atom, cyano, nitro, $C_{1-6}$alkyl, $C_{2-6}$alkenyl, $C_{3-7}$cycloalkyl, $C_{3-7}$cycloalkylC$_{1-4}$alkyl, fluoroC$_{1-6}$alkyl, —(C$_m$H$_{2m}$)R$^9$, —(CH$_2$)$_n$COR$^{10}$ or —(CH$_2$)$_p$NR$^{11}$COR$^{12}$;

$R^9$ represents hydroxy or $C_{1-6}$alkoxy;

$R^{10}$ represents a hydrogen atom, hydroxy, $C_{1-6}$alkyl, $C_{1-6}$alkoxy, phenyl, phenoxy or a group —NR$^{15}$R$^{16}$;

$R^{11}$ represents a hydrogen atom or $C_{1-6}$alkyl;

$R^{12}$ represents a hydrogen atom, $C_{1-6}$alkyl, $C_{1-6}$alkoxy, phenyl, phenoxy, or a group —NR$^{15}$R$^{16}$;

$R^{15}$ and $R^{16}$, which may be the same or different, each independently represent a hydrogen atom or $C_{1-4}$alkyl;

m represents an integer from 1 to 6;

n represents zero or an integer from 1 to 4; and p represents an integer from 1 to 4.

2. A compound of formula (I)

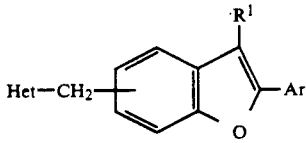 (I)

or a physiologically acceptable salt, solvate or metabolically labile ester thereof wherein $R^1$ represents a hydrogen atom, a halogen atom, $C_{1-6}$alkyl, $C_{2-6}$alkenyl, fluoro$C_{1-6}$alkyl, $C_{1-6}$alkoxy, —CHO, —$CO_2H$ or —$COR^2$;

Ar represents the group

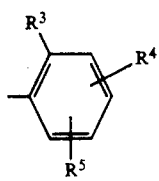

$R^2$ represents $C_{1-6}$alkyl, $C_{2-6}$alkenyl, $C_{1-6}$alkoxy or a group —$NR^{15}R^{16}$;

$R^3$ represents —$CO_2H$, —$NHSO_2CF_3$ or a C-linked tetrazolyl group;

$R^4$ and $R^5$ which may be the same or different each independently represent a hydrogen atom, a halogen atom or $C_{1-6}$alkyl;

Het represents the group

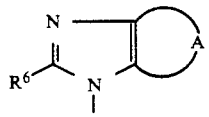

A, when read in a clockwise or anti-clockwise direction, represents

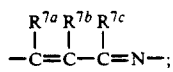

$R^6$ represents a hydrogen atom, $C_{1-6}$alkyl, $C_{2-6}$alkenyl, $C_{1-6}$alkylthio, $C_{1-6}$alkoxy, $C_{3-7}$cycloalkyl, or $C_{3-7}$cycloalkyl$C_{1-4}$alkyl;

$R^{7a}$, $R^{7b}$ and $R^{7c}$, which may be the same or different, each independently represents a hydrogen atom, a halogen atom, cyano, nitro, $C_{1-6}$alkyl, $C_{2-6}$alkenyl, $C_{3-7}$cycloalkyl, $C_{3-7}$cycloalkyl$C_{1-4}$alkyl, fluoro$C_{1-6}$alkyl, —$(C_mH_{2m})R^9$, —$(CH_2)_nCOR^{10}$ or —$(CH_2)_pNR^{11}COR^{12}$;

$R^9$ represents hydroxy or $C_{1-6}$alkoxy;

$R^{10}$ represents a hydrogen atom, hydroxy, $C_{1-6}$alkyl, $C_{1-6}$alkoxy, phenyl, phenoxy or a group —$NR^{15}R^{16}$;

$R^{11}$ represents a hydrogen atom or $C_{1-6}$alkyl;

$R^{12}$ represents a hydrogen atom, $C_{1-6}$alkyl, $C_{1-6}$alkoxy, phenyl, phenoxy, or a group —$NR^{15}R^{16}$;

$R^{15}$ and $R^{16}$, which may be the same or different, each independently represent a hydrogen atom or $C_{1-4}$alkyl;

m represents an integer from 1 to 4;

n represents zero or an integer from 1 to 4; and p represents an integer from 1 to 4.

3. A compound according to claim 1 wherein $R^6$ represents a hydrogen atom, $C_{1-5}$alkyl, $C_{3-5}$alkenyl, $C_{1-5}$alkoxy, $C_{3-5}$cycloalkyl or $C_{3-5}$cycloalkyl$C_{1-2}$alkyl.

4. A compound according to claim 3 wherein $R^6$ represents $C_{2-4}$alkyl.

5. A compound according to claim 4 wherein $R^6$ represents ethyl, n-propyl or n-butyl.

6. A compound according to claim 1 wherein $R^{7a}$, $R^{7b}$ and $R^{7c}$ each independently represent a hydrogen atom, a halogen atom, $C_{1-6}$alkyl, $C_{3-7}$cycloalkyl, $C_{3-7}$cycloalkyl$C_{1-4}$alkyl, —$(CH_2)_mR^9$ or —$(CH_2)_nCOR^{10}$.

7. A compound according to claim 6 wherein $R^9$ represents hydroxy or $C_{1-6}$alkoxy, and $R^{10}$ represents a hydrogen atom, hydroxy, $C_{1-6}$alkoxy or —$NR^{15}R^{16}$, wherein $R^{15}$ and $R^{16}$ each independently represent a hydrogen atom or $C_{1-4}$alkyl, and m is 1 or 2 and n is zero, 1 or 2.

8. A compound according to claim 7 wherein $R^9$ represents hydroxy, methoxy, ethoxy, propoxy or butoxy.

9. A compound according to claim 8 wherein $R^9$ represents hydroxy or methoxy.

10. A compound according to claim 7 wherein $R^{10}$ represents a hydrogen atom, hydroxy, methoxy, ethoxy, propoxy or butoxy.

11. A compound according to claim 10 wherein $R^{10}$ represents a hydrogen atom, hydroxy or methoxy.

12. A compound according to claim 1 wherein the group Het—$CH_2$— is attached at the 5- or 6-position on the benzofuran ring.

13. A compound according to claim 12 wherein the group Het—$CH_2$— is attached at the 5-position on the benzofuran ring.

14. A compound according to claim 1 wherein $R^1$ represents a hydrogen atom, a halogen atom, $C_{1-6}$alkyl, $C_{1-6}$alkoxy or fluoro$C_{1-6}$alkyl.

15. A compound according to claim 14 wherein $R^1$ represents a halogen atom.

16. A compound according to claim 15 wherein $R^1$ represents a bromine atom.

17. A compound according to claim 1 wherein $R^4$ and $R^5$ each independently represent a hydrogen atom or a halogen atom.

18. A compound according to claim 17 wherein $R^4$ and $R^5$ each represent a hydrogen atom.

19. A compound of formula (I)

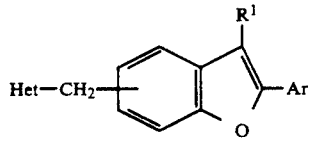 (I)

or a physiologically acceptable salt, solvate or metabolically labile ester thereof wherein $R^1$ represents a halogen atom or fluoro$C_{1-6}$alkyl;

Ar represents the group

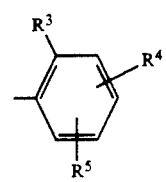

$R^3$ represents $-CO_2H$, $-NHSO_2CF_3$ or a C-linked tetrazolyl group;

$R^4$ and $R^5$ which may be the same or different each independently represent a hydrogen atom, a halogen atom or $C_{1-6}$alkyl;

Het represents the group

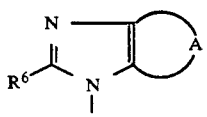

A, when read in a clockwise or anti-clockwise direction, represents

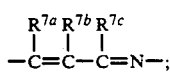

$R^6$ represents a hydrogen atom, $C_{1-6}$alkyl or $C_{3-7}$cycloalkyl;

$R^{7a}$, $R^{7b}$ and $R^{7c}$, which may be the same or different, each independently represents a hydrogen atom, a halogen atom, $C_{1-6}$alkyl, $-(C_mH_{2m})R^9$, or $-(CH_2)_nCOR^{10}$;

$R^9$ represents hydroxy;

$R^{10}$ represents hydroxy, $C_{1-6}$alkoxy or a group $-NR^{15}R^{16}$;

$R^{15}$ and $R^{16}$, which may be the same or different, each independently represent a hydrogen atom or $C_{1-4}$alkyl;

m represents an integer from 1 to 6; and n represents zero or an integer from 1 to 4.

20. A compound selected from

3-[[3-bromo-2-[2-(1H-tetrazol-5-yl)phenyl]-5-benzofuranyl]methyl]-2-ethyl-5,7-dimethyl-3H-imidazo[4,5-b]pyridine;

3-[[3-bromo-2-[2-(1H-tetrazol-5-yl)phenyl]-5-benzofuranyl]methyl]-2-ethyl-5-methyl-3H-imidazo[4,5-b]pyridine;

3-[[3-bromo-2-[2-(1H-tetrazol-5-yl)phenyl]-5-benzofuranyl]methyl]-2-ethyl-7-methyl-3H-imidazo[4,5-b]pyridine-5-carboxylic acid;

3-[[3-bromo-2-[2-(1H-tetrazol-5-yl)phenyl]-5-benzofuranyl]methyl]-5,7-dimethyl-2-propyl-3H-imidazo[4,5-b]pyridine;

3-[[3-bromo-2-[2-(1H-tetrazol-5-yl)phenyl]-5-benzofuranyl]methyl]-7-methyl-2-propyl-3H-imidazo[4,5-b]pyridine-5-carboxylic acid;

3-[[3-bromo-2-[2-(1H-tetrazol-5-yl)phenyl]-5-benzofuranyl]methyl]-2-propyl-3H-imidazo[4,5-b]pyridine-5-carboxylic acid;

3-[[3-bromo-2-[2-(1H-tetrazol-5-yl)phenyl]-5-benzofuranyl]methyl]-2-ethyl-3H-imidazo[4,5-b]pyridine-5-carboxylic acid;

3-[[3-bromo-2-[2-[[(trifluoromethyl)sulphonyl]amino]phenyl]-5-benzofuranyl]-methyl]-2-ethyl-7-methyl-3H-imidazo[4,5-b]pyridine-5-carboxylic acid;

3-[[3-bromo-2-[2-[[(trifluoromethyl)sulphonyl]amino]phenyl]-5-benzofuranyl]methyl]-7-methyl-2-propyl-3H-imidazo[4,5-b]pyridine-5-carboxylic acid;

3-[[3-bromo-2-[2-[[(trifluoromethyl)sulphonyl]amino]phenyl]-5-benzofuranyl]methyl]-2-propyl-3H-imidazo[4,5-b]pyridine-5-carboxylic acid;

3-[[3-bromo-2-[2-[[(trifluoromethyl)sulphonyl]amino]phenyl]-5-benzofuranyl]methyl]-2-ethyl-3H-imidazo[4,5-b]pyridine-5-carboxylic acid;

3-[[3-bromo-2-[2-[[(trifluoromethyl)sulphonyl]amino]phenyl]-5-benzofuranyl]methyl]-2-ethyl-N-methyl-3H-imidazo[4,5-b]pyridine-5-carboxamide;

3-[[3-bromo-2-[2-[[(trifluoromethyl)sulphonyl]amino]phenyl]-5-benzofuranyl]methyl]-N,2-diethyl-3H-imidazo[4,5-b]pyridine-5-carboxamide;

3-[[3-bromo-2-[2-[[(trifluoromethyl)sulphonyl]amino]phenyl]-5-benzofuranyl]methyl]-2-ethyl-3H-imidazo[4,5-b]pyridine-5-carboxamide;

3-[[3-bromo-2-[2-[[(trifluoromethyl)sulphonyl]amino]phenyl]-5-benzofuranyl]methyl]-2-ethyl-N,7-dimethyl-3H-imidazo[4,5-b]pyridine-5-carboxamide;

3-[[3-bromo-2-[2-[[(trifluoromethyl)sulphonyl]amino]phenyl]-5-benzofuranyl]methyl]-N,2-diethyl-7-methyl-3H-imidazo[4,5-b]pyridine-5-carboxamide;

3-[[3-bromo-2-[2-[[(trifluoromethyl)sulphonyl]amino]phenyl]-5-benzofuranyl]methyl]-2-ethyl-7-methyl-3H-imidazo[4,5-b]pyridine-5-carboxamide;

3-[[3-bromo-2-[2-[[(trifluoromethyl)sulphonyl]amino]phenyl]-5-benzofuranyl]methyl]-N-methyl-2-propyl-3H-imidazo[4,5-b]pyridine-5-carboxamide;

3-[[3-bromo-2-[2-[[(trifluoromethyl)sulphonyl]amino]phenyl]-5-benzofuranyl]methyl]-N-ethyl-2-propyl-3H-imidazo[4,5-b]pyridine-5-carboxamide;

3-[[3-bromo-2-[2-[[(trifluoromethyl)sulphonyl]amino]phenyl]-5-benzofuranyl]methyl]-2-propyl-3H-imidazo[4,5-b]pyridine-5-carboxamide;

3-[[3-bromo-2-[2-[[(trifluoromethyl)sulphonyl]amino]phenyl]-5-benzofuranyl]methyl]-N,7-dimethyl-2-propyl-3H-imidazo[4,5-b]pyridine-5-carboxamide;

3-[[3-bromo-2-[2-[[(trifluoromethyl)sulphonyl]amino]phenyl]-5-benzofuranyl]methyl]-N-ethyl-7-methyl-2-propyl-3H-imidazo[4,5-b]pyridine-5-carboxamide;

3-[[3-bromo-2-[2-[[(trifluoromethyl)sulphonyl]amino]phenyl]-5-benzofuranyl]methyl]-7-methyl-2-propyl-3H-imidazo[4,5-b]pyridine-5-carboxamide;

3-[[3-bromo-2-(2-carboxyphenyl)-5-benzofuranyl]methyl]-2-ethyl-3H-imidazo[4,5-b]pyridine-5-carboxylic acid;

2-[3-bromo-5-[(2-ethyl-7-methyl-3H-imidazo[4,5-b]pyridin-3-yl)methyl]-2-benzofuranyl]benzoic acid;

N-[2-[3-bromo-5-[(2-ethyl-7-methyl-3H-imidazo[4,5-b]pyridin-3-yl)methyl]-2-benzofuranyl]phenyl]trifluoromethanesulphonamide;

3-[[3-bromo-2-(2-carboxyphenyl)-5-benzofuranyl]methyl]-2-ethyl-7-methyl-3H-imidazo[4,5-b]pyridine-5-carboxylic acid;

3-[[3-bromo-2-[2-(1H-tetrazol-5-yl)phenyl]-5-benzofuranyl]methyl]-2-ethyl-3H-imidazo[4,5-b]pyridine-5-methanol;

3-[[3-bromo-2-[2-(1H-tetrazol-5-yl)phenyl]-5-benzofuranyl]methyl]-2-ethyl-7-methyl-3H-imidazo[4,5-b]pyridine-5-methanol;

2-[3-bromo-5-[(2-ethyl-5-hydroxymethyl-3H-imidazo[4,5-b]pyridin-3-yl)methyl]-2-benzofuranyl]benzoic acid;

2-[3-bromo-5-[(2-ethyl-5-hydroxymethyl-7-methyl-3H-imidazo[4,5-b]pyridin-3-yl)methyl]-2-benzofuranyl]benzoic acid;

3-[[3-bromo-2-[2-[[(trifluoromethyl)sulphonyl]amino]phenyl]-5-benzofuranyl]methyl]-2-ethyl-3H-imidazo[4,5-b]pyridine-5-methanol;

3-[[3-bromo-2-[2-[[(trifluoromethyl)sulphonyl]amino]phenyl]-5-benzofuranyl]methyl]-2-ethyl-7-methyl-3H-imidazo[4,5-b]pyridine-5-methanol;

or a physiologically acceptable salt, solvate or metabolically labile ester thereof.

21. N-[2-[3-Bromo-5-[(5,7-dimethyl-2-ethyl-3H-imidazo[4,5-b]pyridin-3-yl)methyl]-2-benzofuranyl]-phenyl]trifluoromethanesulphonamide or a physiologically acceptable salt or solvate thereof.

22. A pharmaceutical composition comprising at least one compound of formula (I) as defined in claim 1 or a physiologically acceptable salt, solvate or metabolically labile ester thereof, together with at least one physiologically acceptable carrier or excipient.

23. A compound of formula (I):

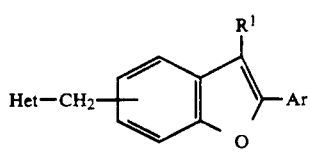

or a physiologically acceptable salt, solvate or metabolically labile ester thereof wherein $R^1$ represents a hydrogen atom, a halogen atom, $C_{1-6}$alkyl, $C_{2-6}$alkenyl, fluoro$C_{1-6}$alkyl, $C_{1-6}$alkoxy, —CHO, —CO$_2$H or —COR$^2$;

Ar represents the group

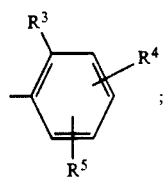

$R^2$ represents $C_{1-6}$alkyl, $C_{2-6}$alkenyl, $C_{1-6}$alkoxy or a group —NR$^{15}$R$^{16}$;

$R^3$ represents —CO$_2$H, —NHSO$_2$CF$_3$ or a C-linked tetrazolyl group;

$R^4$ and $R^5$, which may be the same or different each independently represent a hydrogen atom, a halogen atom or $C_{1-6}$alkyl;

Het represents the group

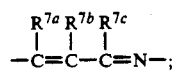

A, when read in a clockwise or anti-clockwise direction, represents $$-\underset{|}{\overset{R^{7a}}{C}}=\underset{|}{\overset{R^{7b}}{C}}-\underset{|}{\overset{R^{7c}}{C}}=N-;$$

$R^6$ represents a hydrogen atom, $C_{1-6}$alkyl, $C_{2-6}$alkenyl, $C_{1-6}$alkylthio, $C_{1-6}$alkoxy, $C_{3-7}$cycloalkyl, or $C_{3-7}$cycloalkyl$C_{1-4}$alkyl;

$R^{7a}$, $R^{7b}$ and $R^{7c}$ each independently represent a hydrogen atom, a chlorine atom, methyl, ethyl, cyclopropyl, cyclopropylmethyl, —CH$_2$OH, —CH$_2$OCH$_3$, —CHO, —CO$_2$H, —CO$_2$CH$_3$, —CO$_2$CH$_2$CH$_3$, —CONH$_2$, —CONHCH$_3$, —CH(CH$_3$)OH or —C(CH$_3$)$_2$OH.

24. A compound according to claim 23 wherein $R^{7a}$, $R^{7b}$ and $R^{7c}$ each independently represent a hydrogen atom, a chlorine atom, methyl, ethyl, cyclopropyl, cyclopropylmethyl, —CH$_2$OH, —CH$_2$OCH$_3$, —CHO, —CO$_2$H, —CO$_2$CH$_3$, —CO$_2$CH$_2$CH$_3$, —CONH$_2$, or —CONHCH$_3$.

25. A compound according to claim 23 wherein $R^{7a}$, $R^{7b}$ and $R^{7c}$ each represent —C(CH$_3$)$_2$OH.

* * * * *